United States Patent [19]

Nargund et al.

[11] Patent Number: 5,767,118
[45] Date of Patent: Jun. 16, 1998

[54] 4-HETEROCYCLIC PEPERIDINES PROMOTE RELEASE OF GROWTH HORMONE

[75] Inventors: Ravi Nargund, East Brunswick; Arthur A. Patchett, Westfield; Lihu Yang, Edison, all of N.J.

[73] Assignee: Merck & Co., Inc., Rahway, N.J.

[21] Appl. No.: 329,357

[22] Filed: Oct. 26, 1994

[51] Int. Cl.⁶ ............... A61K 31/535; A61K 31/54; A01N 43/54; A01N 43/40; C07D 401/00; C07D 409/00; C07D 211/36; C07D 211/68

[52] U.S. Cl. ............... 514/226.4; 514/226.8; 514/227.8; 514/230.5; 514/232.2; 514/259; 514/264; 514/312; 514/314; 514/315; 514/319; 514/320; 514/321; 514/322; 514/323; 514/324; 514/326; 514/338; 514/339; 514/341; 514/342; 514/343; 544/55; 544/60; 544/90; 544/96; 544/111; 544/124; 544/129; 544/235; 544/238; 544/253; 544/284; 544/353; 544/360; 546/188; 546/192; 546/193; 546/197; 546/198; 546/199; 546/200; 546/201; 546/270.1; 546/270.4; 546/271.1; 546/271.4; 546/272.4; 546/273.4; 546/273.7; 546/274.1; 546/274.4; 546/275.7; 546/276.1; 546/283.4; 546/284.1; 546/202; 546/209; 546/210; 546/212; 546/213; 546/268; 546/269; 546/269.7; 546/280.04; 546/282.7

[58] Field of Search ............... 544/360, 153, 544/284, 90, 55, 96, 111, 124, 129, 235, 238, 253, 353; 546/212, 210, 209, 188, 193, 199, 200, 201, 192, 196, 197, 198, 202, 213, 268.7, 269.4, 269.7, 270.1, 270.4, 271.1, 271.4, 272.4, 273.4, 273.7, 274.1, 274.4; 514/230.5, 259, 314, 316, 318, 320, 322, 326

[56] References Cited

U.S. PATENT DOCUMENTS

| | | | |
|---|---|---|---|
| 5,206,235 | 4/1993 | Fisher et al. | 514/213 |
| 5,273,989 | 12/1993 | Schwartz et al. | 514/378 |
| 5,492,916 | 2/1996 | Morriello | 514/323 |
| 5,492,920 | 2/1996 | Chen | 514/323 |
| 5,494,919 | 2/1996 | Morriello | 514/323 |

Primary Examiner—C. Warren Ivy
Assistant Examiner—Raymond Covington
Attorney, Agent, or Firm—J. Eric Thies; David L. Rose

[57] ABSTRACT

The present invention is directed to certain novel compounds identified as 4-heterocycle substituted piperidines of the general structural formula:

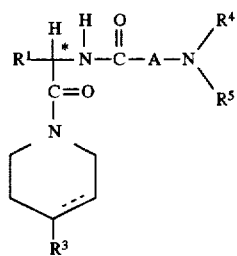

wherein $R^1$, $R^4$, $R^5$, A, $R^3$ and the dashed line are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such compounds as the active ingredient thereof are also disclosed.

11 Claims, No Drawings

4-HETEROCYCLIC PEPERIDINES PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine. L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzolactam structure are disclosed in e.g., U.S. Pat. Nos. 5,206,235, 5,283,241, 5,284,841, 5,310,737 and 5,317,017. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to certain 4-heterocyclic substituted piperidine compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the piperidine compounds. It is a further object of this invention to describe procedures for the preparation of such compounds. A still further object is to describe the use of such compounds to increase the secretion of growth hormone in humans and animals. A still further object of this invention is to describe compositions containing the piperidine compounds for the use of treating humans and animals so as to increase the level of growth hormone secretions. Further objects will become apparent from a reading of the following description.

DESCRIPTION OF THE INVENTION

The novel piperidine compounds of the instant invention are best described in the following structural Formula I:

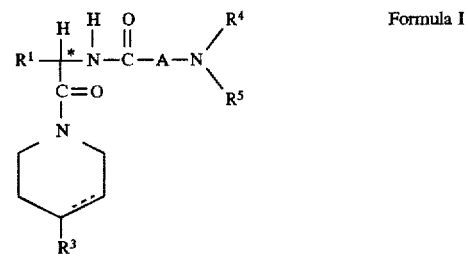

Formula I wherein:

$R^1$ is selected from the group consisting of: $C_1$–$C_{10}$ alkyl, aryl, aryl($C_1$–$C_6$ alkyl), ($C_3$–$C_7$ cycloalkyl)($C_1$–$C_6$ alkyl)-, ($C_1$–$C_5$ alkyl)-K-($C_1$–$C_5$ alkyl)-, aryl($C_0$–$C_5$ alkyl)-K-($C_1$–$C_5$ alkyl)-, and ($C_3$–$C_7$ cycloalkyl)($C_0$–$C_5$ alkyl)-K-($C_1$–$C_5$ alkyl)-, where K is —O—, —S(O)$_m$—, —N($R^2$)C(O)—, —C(O)N($R^2$)—, —OC(O)—, —C(O)O—, —$CR^2$=$CR^2$—, or —C≡C—, where aryl is selected from: phenyl, naphthyl, indolyl, azaindolyl, pyridyl, benzothienyl, benzofuranyl, thiazolyl, and benzimidazolyl, and $R^2$ and alkyl may be further substituted by 1 to 9 halogen, —S(O)$_m$ $R^{2a}$, 1 to 3 of —OR$^{2a}$ or —C(O)OR$^{2a}$, and aryl may be further substituted by 1 to 3 of $C_1$–$C_6$ alkyl, 1 to 3 of halogen, 1 to 2 of —OR$^2$, methylenedioxy, —S(O)$_m$R$^2$, 1 to 2 of —CF$_3$, —OCF$_3$, nitro, —N(R$^2$)C(O)(R$^2$), —C(O)OR$^2$, —C(O)N(R$^2$)(R$^2$), —1H-tetrazol-5-yl, —SO$_2$N(R$^2$)(R$^2$), —N(R$^2$)SO$_2$ phenyl, or —N(R$^2$)SO$_2$R$^2$;

$R^2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or NR$^{3a}$;

$R^{2a}$ is hydrogen, or $C_1$–$C_6$ alkyl optionally substituted by phenyl;

$R^3$ is a heterocycle selected from the group consisting of:

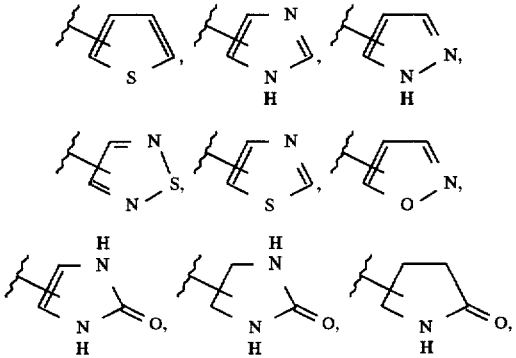

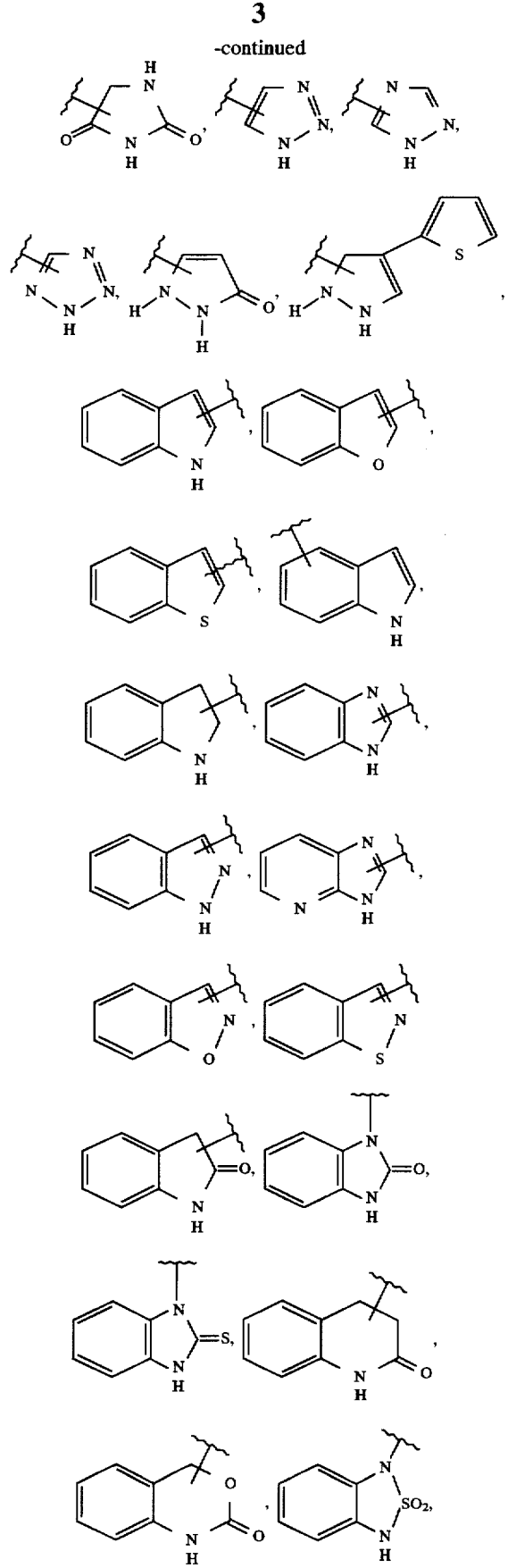

where the heterocycle is attached to the piperidine ring at an available nitrogen or carbon atom of the heterocycle, and where the heterocycle is optionally substituted on at least one available nitrogen or carbon atom by $—R^8$, $—OR^8$, $—SR^8$, or $—N(R^2)(R^8)$ where $R^8$ is independently selected from the group consisting of:

hydrogen, $C_1$-$C_6$ alkyl, halogen, $—OR^2$, $—OR^6$, $—NHSO_2CF_3$, $—(CH_2)_r OR^6$, $—(CH_2)_r N(R^2)(R^6)$, $—(CH_2)_r(R^6)$, $—(CH_2)_r C(O)OR^2$, $—(CH_2)_r C(O)OR^6$, $—(CH_2)_r OC(O)R^2$, $—(CH_2)_r OC(O)R^6$, $—(CH_2)_r C(O)R^2$, $—(CH_2)_r C(O)R^6$, $(CH_2)_r C(O)N(R^2)(R^2)$, $—(CH_2)_r C(O)N(R^2)(R^6)$, $—(CH_2)_r N(R^2)C(O)R^2$, $—(CH_2)_r N(R^2)C(O)R^6$, $—(CH_2)_r N(R^6)C(O)R^2$, $—(CH_2)_r N(R^6)C(O)R^6$, $—(CH_2)_r N(R^2)C(O)OR^2$, $—(CH_2)_r N(R^2)C(O)OR^6$, $—(CH_2)_r N(R^6)C(O)OR^2$, $—(CH_2)_r N(R^6)C(O)OR^6$, $(CH_2)_r N(R^2)C(O)N(R^2)(R^6)$, $—(CH_2)_r N(R^2)C(O)N(R^2)(R^2)$, $—(CH_2)_r N(R^6)C(O)N(R^2)(R^6)$, $—(CH_2)_r N(R^2)SO_2R^6$, $—(CH_2)_r N(R^2)SO_2R^2$, $—(CH_2)_r N(R^6)SO_2R^2$, $—(CH_2)_r N(R^6)SO_2R^6$, $(CH_2)_r OC(O)N(R^2)(R^6)$, $—(CH_2)_r OC(O)N(R^2)(R^2)$, $—(CH_2)_r SO2N(R^2)(R^6)$, $—(CH_2)_r SO_2N(R^2)(R^2)$, $—(CH_2)_r SO_2NHC(O)R^6$, $—(CH_2)_r SO_2NHC(O)R^2$, $—(CH_2)_r SO_2NHC(O)OR^6$, $—(CH_2)_r SO_2NHC(O)OR^2$, $—(CH_2)_r C(O)NHC(O)N(R^2)(R^6)$, $—(CH_2)_r C(O)NHC(O)N(R^2)(R^2)$, $—(CH_2)_r C(O)NHC(O)R^6$, $—(CH_2)_r CONHC(O)R^2$, $—(CH_2)_r CONHSO_2R^6$, $—(CH_2)_r CONHSO_2R^2$, $—(CH_2)_r CONHSO_2N(R^2)R^2)$, $—(CH_2)_r CONHSO_2N(R^2)R^6)$, $—(CH_2)_r N(R^2)SO_2N(R^2)R^6)$, $—(CH_2)_r N(R^6)SO_2N(R^2)R^6)$, $—(CH_2)_r S(O)_m R^6$, and $—(CH_2)_r S(O)_m R^2$;

$R^{3a}$ is hydrogen, or $C_1$-$C_6$ alkyl optionally substituted by hydroxyl;

$R^4$ and $R^5$ are independently hydrogen, $C_1$-$C_6$ alkyl, substituted $C_1$-$C_6$ alkyl where the substituents may be 1 to 5 halo, 1 to 3 hydroxy, 1 to 3 $C_1$-$C_{10}$ alkanoyloxy, 1 to 3 $C_1$-$C_6$ alkoxy, phenyl, phenoxy, 2-furyl, $C_1$-$C_6$ alkoxycarbonyl, $S(O)_m(C_1$-$C_6$ alkyl); or $R^4$ and $R^5$ can be taken together to form $—(CH_2)_d L_a(CH_2)_e—$ where $L_a$ is $C(R^2)_2$, $O$, $S(O)_m$ or $N(R^2)$, d and e are independently 1 to 3 and $R^2$ is as defined above;

A is:

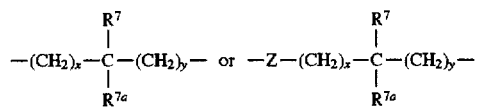

where x and y are independently 0, 1, 2 or 3;

Z is N-R$^{6a}$ or O, where R$^6$a is hydrogen or C$_1$-C$_6$ alkyl;

R$^6$ is hydrogen, C$_1$-C$_6$ alkyl, or (CH$_2$)$_v$aryl, wherein the alkyl and (CH$_2$)$_v$ groups may be optionally substituted by 1-2 O(R$^2$), S(O)$_m$R$^2$, 1H-tetrazol-5-yl, C(O)OR$^2$, C(O)N(R$^2$)(R$^2$), or SO$_2$N(R$^2$)(R$^2$), N(R$^2$)C(O)N(R$^2$)(R$^2$), and where aryl is phenyl, pyridyl, 1H-tetrazol-5-yl, triazolyl, imidazolyl, thiazolyl, pyrazolyl, thiadiazolyl, imidazolone-1-yl, oxadiazolyl, benzimidazol-2-yl, triazolinone-yl, optionally substituted with C$_1$-C$_6$ alkyl, C$_3$-C$_6$ cycloalkyl, amino, or hydroxyl;

R$^7$ and R$^{7a}$ are independently hydrogen, C$_1$-C$_6$ alkyl, trifluoromethyl, phenyl, substituted C$_1$-C$_6$ alkyl where the substituents are imidazolyl, phenyl, indolyl, p-hydroxyphenyl, OR$^2$, S(O)$_m$R$^2$, C(O)OR$^2$, C$_3$-C$_7$ cycloalkyl, N(R$^2$)(R$^2$), C(O)N(R$^2$)(R$^2$); or R$^7$ and R$^{7a}$ can independently be joined to one or both of R$^4$ and R$^5$ groups to form alkylene bridges between the terminal nitrogen and the alkyl portion of the R$^7$ or R$^{7a}$ groups, wherein the bridge contains 1 to 5 carbons atoms; or R$^7$ and R$^7$a can be joined to one another to form a C$_3$-C$_7$ cycloalkyl;

m is 0, 1, or 2;

r is 0, 1, 2, or 3;

v is 0, 1, or 2;

the dashed line indicates the presence of either a single bond or a double bond between the specified carbon atoms;

and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl (Me), ethyl (Et), propyl (Pr), isopropyl (i-Pr), butyl (Bu), sec-butyl (s-Bu), tertiary butyl (t-Bu), pentyl, isopentyl, hexyl, isohexyl, allyl, propinyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propinyloxy, isobutenyloxy, hexenyloxy and the like. The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of C$_1$-C$_6$ alkyl, 1 to 3 of halogen, 1 to 2 of —OR$^2$, methylenedioxy, —S(O)$_m$R$^2$, 1 to 2 of -CF$_3$, -OCF$_3$, nitro, —N(R$^2$)C(O)(R$^2$), —C(O)OR$^2$, —C(O)N(R$^2$)(R$^2$), —1H-tetrazol-5-yl, —SO$_2$N(R$^2$)(R$^2$), —N(R$^2$)SO$_2$ phenyl, or —N(R$^2$)SO$_2$R$^2$, wherein R$^2$ is as defined herein.

Certain of the above defined terms may occur more than once in the above formula or definitions and upon such occurrence, each term shall be defined independently of the other.

Preferred compounds of the instant invention include those of Formula Ia:

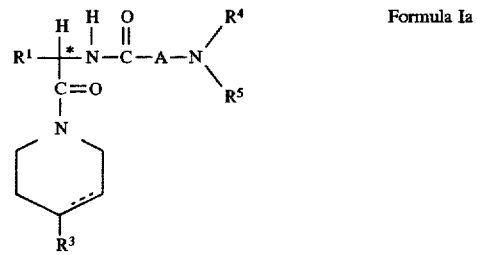

Formula Ia wherein:

R$^1$ is selected from the group consisting of: C$_1$-C$_{10}$ alkyl, aryl (C$_1$-C$_4$ alkyl)-, C$_3$-C$_6$ cycloalkyl (C$_1$-C$_4$ alkyl)-, (C$_1$-C$_4$ alkyl)-K-(C$_1$-C$_2$ alkyl)-, aryl (C$_0$-C$_2$ alkyl)-K-(C$_1$-C$_2$ alkyl)-, and (C$_3$-C$_7$ cycloalkyl)(C$_0$-C$_2$ alkyl)-K-(C$_1$-C$_2$ alkyl)-, where K is —O—, —S(O)$_m$—, —OC(O)—, or —C(O)O—, and the alkyl groups may be further substituted by 1 to 7 halogen, —S(O)$_m$R$^2$, 1 to 3 —OR$^2$ or -C(O)OR$^2$, and aryl is phenyl, naphthyl, indolyl, pyridyl, benzimidazolyl, azaindolyl, benzothienyl or benzofuranyl which may be further substituted by 1 to 2 C$_1$-C$_4$ alkyl, 1 to 2 halogen, 1 to 2 —OR$^2$, —S(O)$_m$R$^2$, or —C(O)OR$^2$;

R$^2$ is hydrogen, C$_1$-C$_6$ alkyl, C$_3$-C$_7$ cycloalkyl and where two C$_1$-C$_6$ alkyl groups are present on one atom they may be optionally joined to form a C$_4$-C$_7$ cyclic ring optionally including oxygen, sulfur or NR$^3$a;

R$^3$ is a heterocycle selected from the group consisting of:

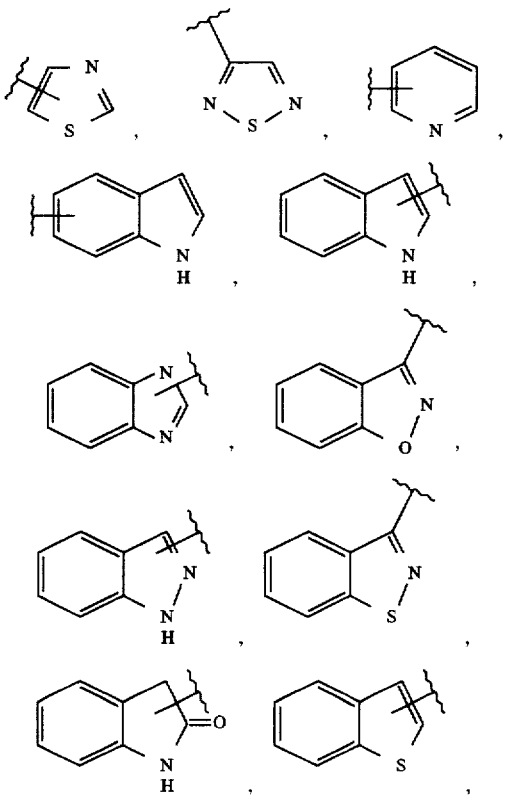

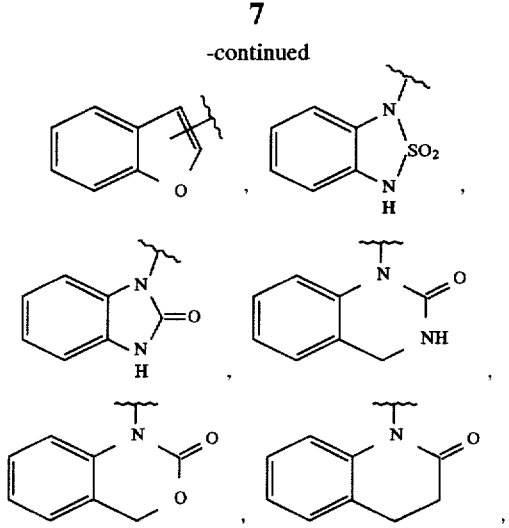

where the heterocycle is optionally substituted on at least one available nitrogen or carbon atom by —R$^8$ or —OR$^8$, where R$^8$ is independently selected from the group consisting of: hydrogen, C$_1$–C$_6$ alkyl, halogen, —OR$^2$, —OR$^6$, —NHSO$_2$CF$_3$, —(CH$_2$)$_r$OR$^6$, —(CH$_2$)$_r$N(R$^2$)(R$^6$), —(CH$_2$)$_r$(R$^6$), —(CH$_2$)$_r$C(O)OR$^2$, —(CH$_2$)$_r$C(O)OR$^6$, —(CH$_2$)$_r$OC(O)R$^2$, —(CH$_2$)$_r$OC(O)R$^6$, —(CH$_2$)$_r$C(O)R$^2$, —(CH$_2$)$_r$C(O)R$^6$, (CH$_2$)$_r$C(O)N(R$^2$)(R$^2$), —(CH$_2$)$_r$C(O)N(R$^2$)(R$^6$), —(CH$_2$)$_r$N(R$^2$)C(O)R$^2$, —(CH$_2$)$_r$N(R$^2$)C(O)R$^6$, —(CH$_2$)$_r$N(R$^6$)C(O)R$^2$, —(CH$_2$)$_r$N(R$^6$)C(O)R$^6$, —(CH$_2$)$_r$N(R$^2$)C(O)OR$^2$, —(CH$_2$)$_r$N(R$^6$)C(O)OR$^6$, —(CH$_2$)$_r$N(R$^6$)C(O)OR$^2$, —(CH$_2$)$_r$N(R$^2$)C(O)OR$^6$, —(CH$_2$)$_r$N(R$^2$)C(O)N(R$^2$)(R$^6$), —(CH$_2$)$_r$N(R$^6$)C(O)N(R$^2$)(R$^6$), —(CH$_2$)$_r$N(R$^2$)SO$_2$R$^6$, —(CH$_2$)$_r$N(R$^2$)SO$_2$R$^2$, —(CH$_2$)$_r$N(R$^6$)SO$_2$R$^2$, —(CH$_2$)$_r$N(R$^6$)SO$_2$R$^6$, (CH$_2$)$_r$OC(O)N(R$^2$)(R$^6$), —(CH$_2$)$_r$OC(O)N(R$^2$)(R$^2$), —(CH$_2$)$_r$SO$_2$N(R$^2$)(R$^6$), —(CH$_2$)$_r$SO$_2$N(R$^2$)(R$^2$), —(CH$_2$)$_r$SO$_2$NHC(O)R$^6$, (CH$_2$)$_r$SO$_2$NHC(O)R$^2$, —(CH$_2$)$_r$SO$_2$NHC(O)OR$^6$, —(CH$_2$)$_r$SO$_2$NHC(O)OR$^2$, —(CH$_2$)$_r$C(O)NHC(O)N(R$^2$)(R$^6$), —(CH$_2$)$_r$C(O)NHC(O)N(R$^2$)(R$^2$), —(CH$_2$)$_r$C(O)NHC(O)R$^6$, —(CH$_2$)$_r$CONHC(O)R$^2$, —(CH$_2$)$_r$CONHSO$_2$R$^6$,—(CH$_2$)$_r$CONHSO$_2$R$^2$, (CH$_2$)$_r$CONHSO$_2$N(R$^2$)R$^2$), —(CH$_2$)$_r$CONHSO$_2$N(R$^2$)R$^6$), —(CH$_2$)$_r$N(R$^2$)SO$_2$N(R$^2$)R$^6$), —(CH$_2$)$_r$N(R$^6$)SO$_2$N(R$^2$)R$^6$), —(CH$_2$)$_r$S(O)$_m$R$^6$, and —(CH$_2$)$_r$S(O)$_m$R$^2$;

R$^{3a}$ is hydrogen, or C$_1$–C$_4$ alkyl;

R$^4$ and R$^5$ are independently hydrogen, C$_1$–C$_6$ alkyl, or substituted C$_1$–C$_6$ alkyl where the substituents may be 1 to 5 halo, 1 to 3 hydroxyl, S(O)$_m$(C$_1$–C$_6$ alkyl) or phenyl;

R$^6$ is H, C$_1$–C$_6$ alkyl, or (CH$_2$)$_v$aryl, wherein the (CH$_2$)$_v$ and alkyl groups may be optionally substituted by 1–2 O(R$^2$), S(O)$_m$R$^2$, C(O)OR$^2$, C(O)N(R$^2$)(R$^2$) or SO$_2$N(R$^2$)(R$^2$), N(R$^2$)C(O)N(R$^2$)(R$^2$), wherein the aryl group is selected from: phenyl, pyridyl, 1H-tetrazol-5-yl, triazolyl, imidazolyl, thiazolyl, oxadiazolyl, pyrazolyl, thiadiazolyl, and benzimidazol-2-yl, which is optionally substituted with C$_1$–C$_6$ alkyl, C$_3$–C$_6$ cycloalkyl, amino, or hydroxyl;

A is:

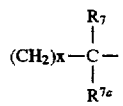

where x is 0, or 1;

R$^7$ and R$^{7a}$ are independently hydrogen C$_1$–C$_6$ alkyl, trifluoromethyl, phenyl, substituted C$_1$–C$_6$ alkyl where the substituents are imidazolyl, phenyl, indolyl, p-hydroxyphenyl, OR$^2$, S(O)$_m$R$^2$, C(O)OR$^2$, C$_5$–C$_7$ cycloalkyl, N(R$^2$)(R$^2$), C(O)N(R$^2$)(R$^2$); or R$^7$ and R$^{7a}$ can independently be joined to one of R$^4$ or R$^5$ to form alkylene bridges between the terminal nitrogen and the alkyl portion of R$^7$ or R$^{7a}$ groups to form 5 or 6 membered rings; or R$^7$ and R$^{7a}$ can be joined to one another to form a C$_3$ cycloalkyl;

m is 0, 1, or 2;

r is 0, 1, 2, or 3;

v is 0, 1, or 2;

the dashed line indicates the presence of either a single bond or a double bond between the specified carbon atoms;

and pharmaceutically acceptable salts and individual diastereomers thereof.

The most preferred compounds of the present invention include the following:

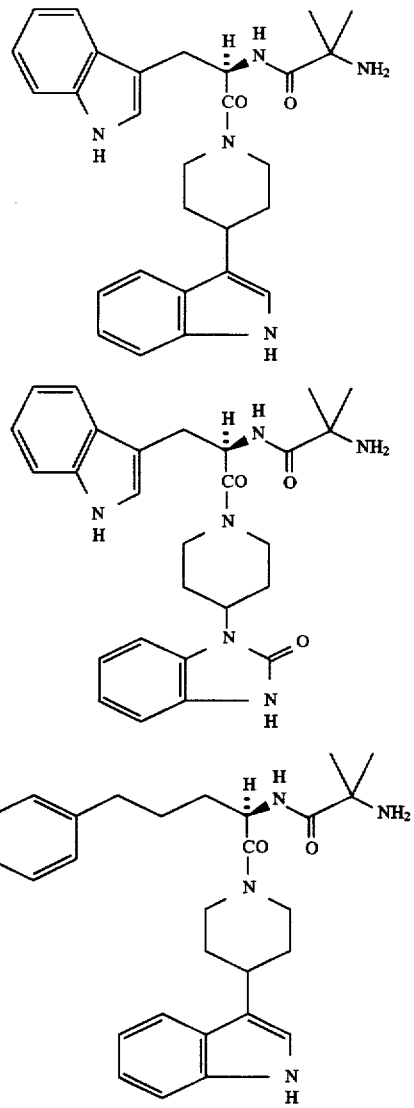

-continued
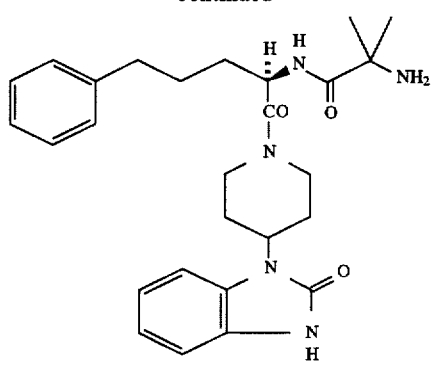
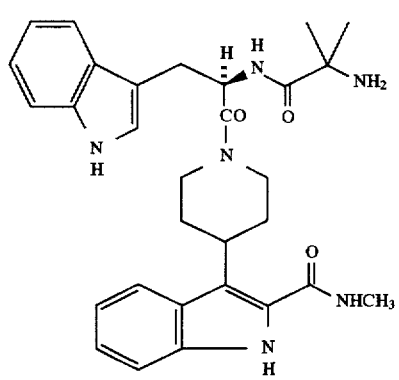
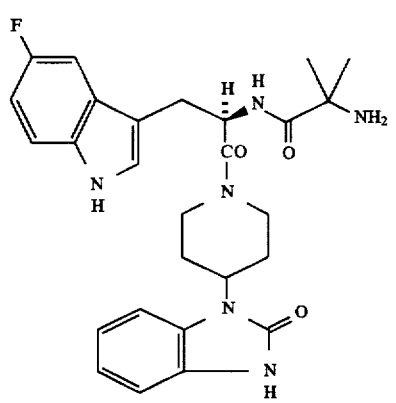
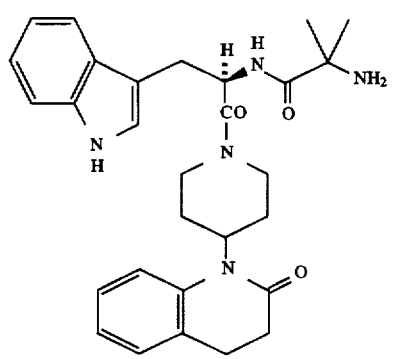
-continued
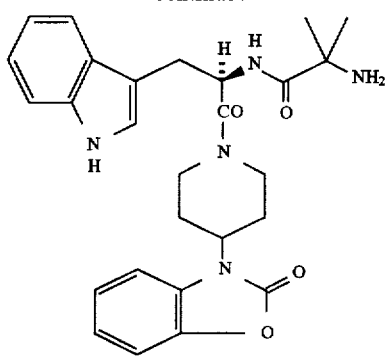
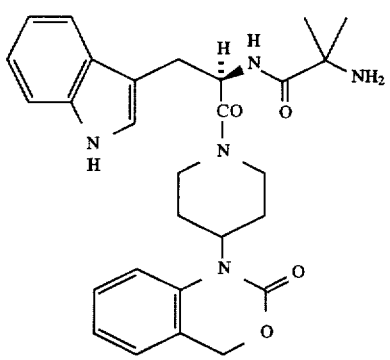
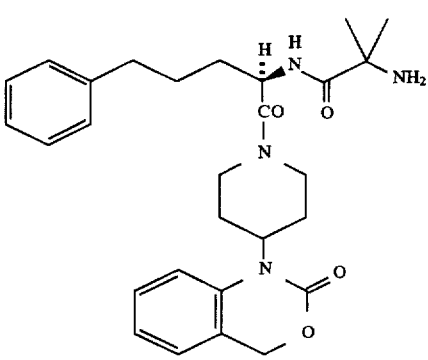
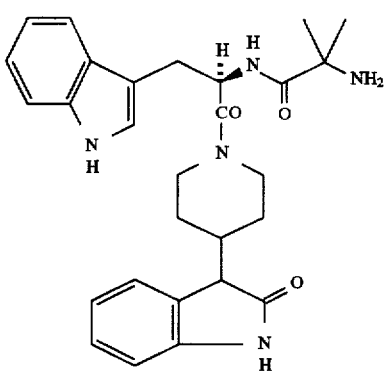

-continued
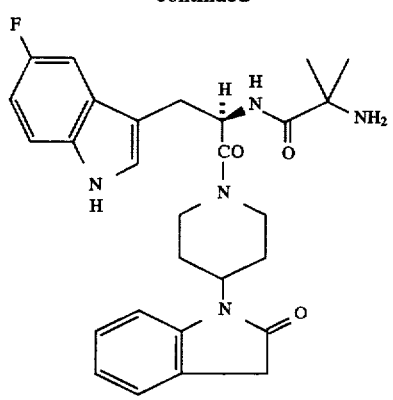
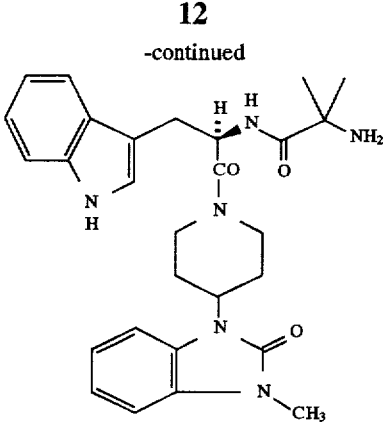
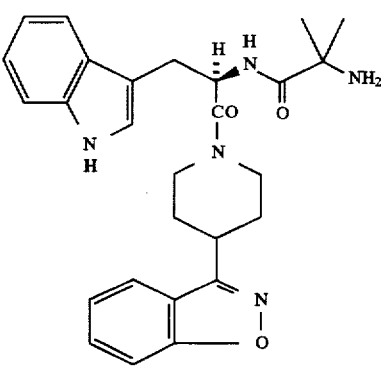
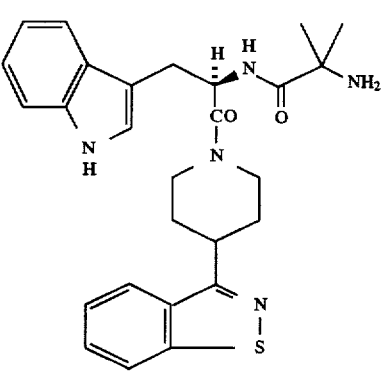
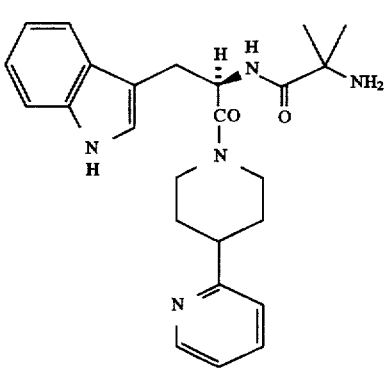

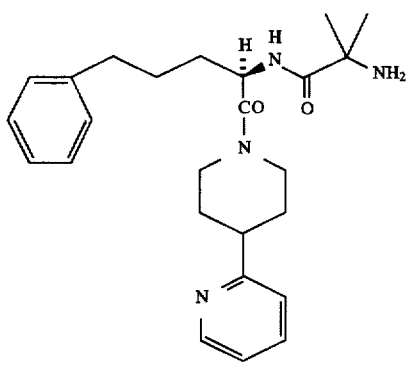

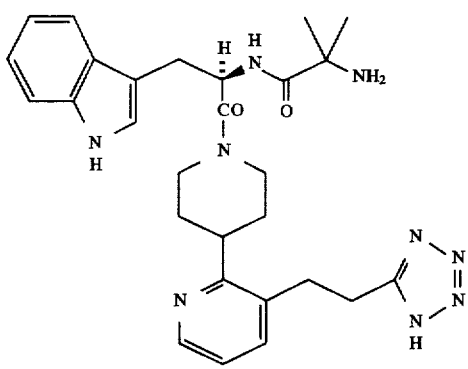

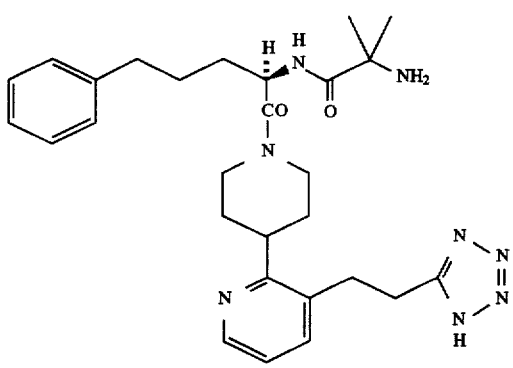

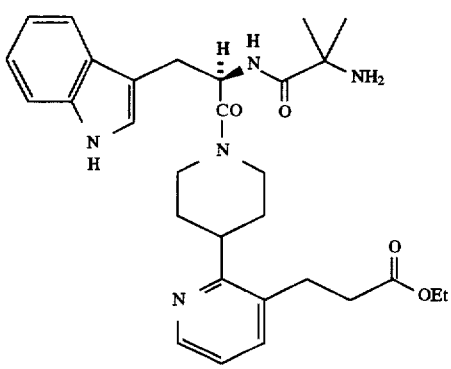

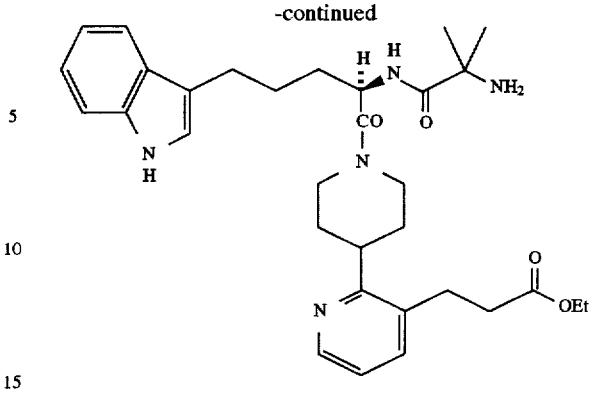

and their pharmaceutically acceptable salts and individual diasteromers thereof, where not otherwise specified.

All of the most preferred compounds shown above have an asymmetric center, which is shown in its preferred (R)-stereochemistry.

Throughout the instant application, the following abbreviations are used with the following meanings:

| | |
|---|---|
| BOC | t-butyloxycarbonyl |
| BOP | Benzotriazol-1-yloxy tris(dimethylamino)-phosphonium hexafluorophosphate |
| CBZ | Benzyloxycarbonyl |
| DIBAL-H | diisobutylaluminum hydride |
| DMF | N,N-dimethylformamide |
| EDC | 1-(3-dimethylaminopropyl)-3-ethylcarbodiimide hydrochloride |
| FAB-MS | Fast atom bombardment-mass spectroscopy |
| GHRP | Growth hormone releasing peptide |
| HOBT | Hydroxybenztriazole |
| LAH | Lithium aluminum hydride |
| HPLC | High pressure liquid chromatography |
| MHz | Megahertz |
| MPLC | Medium pressure liquid chromatography |
| NMM | N-Methylmorpholine |
| NMR | Nuclear Magnetic Resonance |
| PLC | Preparative liquid chromatography |
| RPLC | Reverse phase liquid chromatography |
| TFA | Trifluoroacetic acid |
| THF | Tetrahydrofuran |
| TLC | Thin layer chromatography |
| TMS | Tetramethylsilane |

The compounds of the instant invention all have at least one asymmetric center as noted by the asterisk in the structural Formula I:

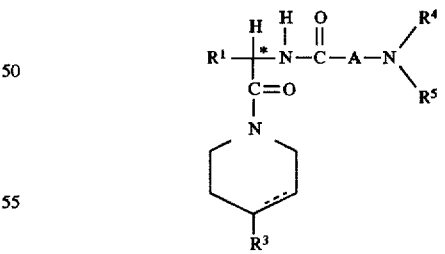

Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention.

Compounds which are more active as growth hormone secretagogues and, therefore are preferred, are those in which the nitrogen substituent is above and the hydrogen atom is below the plane of the structure as represented in Formula II. An equivalent representation places $R^1$ and the N-substituent in the plane of the structure with the C=O group above the plane of the structure.

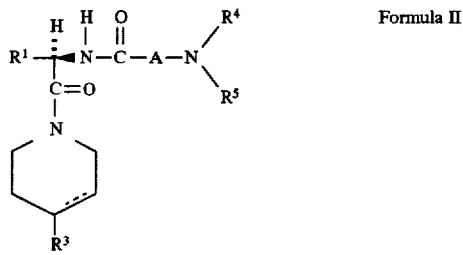

Formula II

This configuration corresponds to that present in a D-amino acid. In most cases, this is also designated as an R-configuration although this will vary according to the value of $R_1$ used in making the R- or S- stereochemical assignments. Their absolute stereochemistry may be determined by the X-ray crystallography of crystalline products or crystalline intermediates which are derivatized, if necessary, containing an asymmetric center of known configuration.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention can be carried out in sequential or convergent synthetic routes. Syntheses detailing the preparation of the compounds of Formula I in a sequential manner are presented in the following reaction schemes.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present are found in Greene, T; Wuts, P. G. M. *Protective Groups in Organic Synthesis*, John Wiley & Sons, Inc., New York, N.Y. (1991). CBZ and BOC were used extensively in the syntheses of this invention, and their removal conditions are known to those skilled in the art. Removal of CBZ groups can be achieved by a number of methods, for example, catalytic hydrogenation with hydrogen in the presence of palladium catalyst in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol, with a strong acid, such as trifluoroacetic acid (TFA) or hydrochloric acid (HCl).

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids*, Pergamon Press: Oxford, 1989). Many of the piperidines of formula 2 are either commercially available or known in the literature and others can be prepared following literature methods, some of which are described here. The skills required in carrying out the reaction and purification of the resulting reaction products are known to those skilled in the art. Purification procedures include crystallization, normal phase or reverse phase chromatography.

SCHEME 1

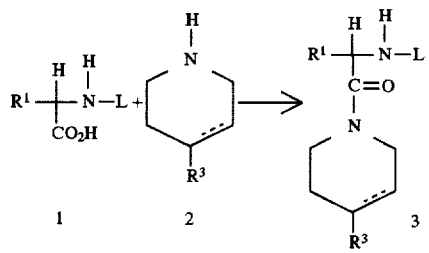

Intermediates of formula 3 can be synthesized as described in Scheme 1. Coupling of amine of formula 2, whose preparations are described later if they are not commercially available, to protected amino acids of formula 1, wherein L is a suitable protecting group, is conveniently carried out under standard peptide coupling conditions.

SCHEME 2

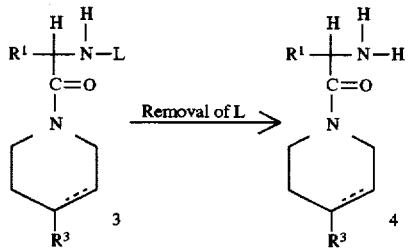

Conversion of 3 to intermediates 4 can be carried out as illustrated in Scheme 2 by removal of the protecting group L (CBZ, BOC, etc.)

SCHEME 3

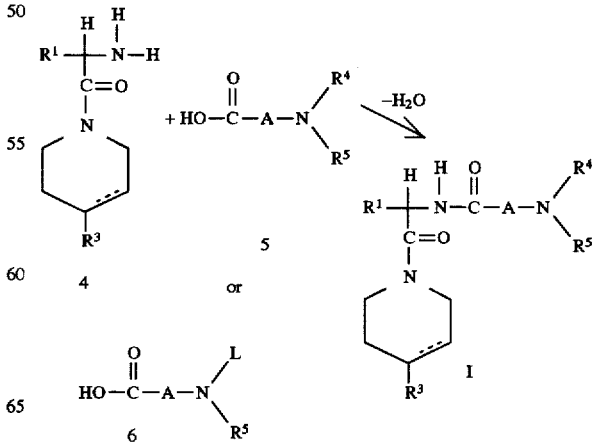

SCHEME 3
-continued

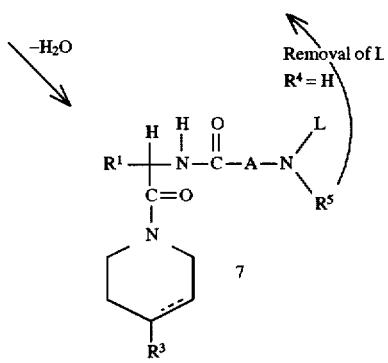

Intermediates of formula 5, wherein A is connected to the carbonyl by a carbon atom —(CH$_2$)$_x$CR$^7$R$^{7a}$(CH$_2$)$_y$- as shown in Scheme 3 can be coupled to intermediates of formula 4 under the standard peptide coupling reaction conditions. The amino acids 5, as amino acids 1, are either commercially available or may be synthesized. Also if R$^4$ or R$^5$ is a hydrogen then the protected amino acids 6 are employed in the coupling reaction, wherein L is a protecting group as defined above. Removal of L in 7 to afford I, where R$^4$=H, can be carried out under conditions known in the art.

SCHEME 4

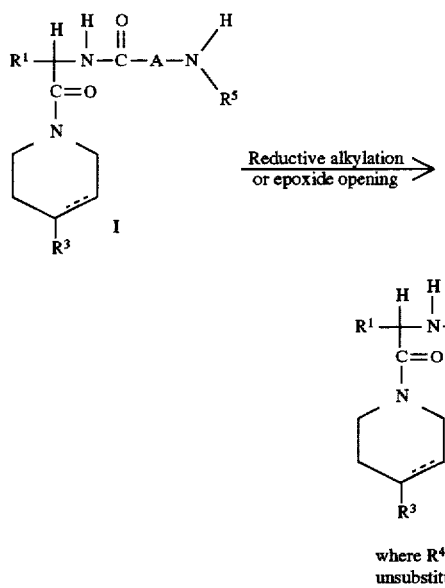

where R$^4$ is substituted/unsubstituted alkyl

Compounds of formula I wherein R$^4$ and/or R$^5$ is a hydrogen can be further elaborated to new compounds I (with most preferred side chains R$^4$=CH$_2$-CH(OH)-CH$_2$X, wherein X=H or OH) which are substituted on the amino group as depicted in Scheme 4. Reductive alkylation of I with an aldehyde is carried out under conditions known in the art; for example, by catalytic hydrogenation with hydrogen in the presence of platinum, palladium, or nickel catalysts or with chemical reducing agents such as sodium cyanoborohydride in a protic solvent such as methanol or ethanol in the present of catalytic amount of acid. Alternatively, a similar transformation can be accomplished via an epoxide opening reaction.

SCHEME 5

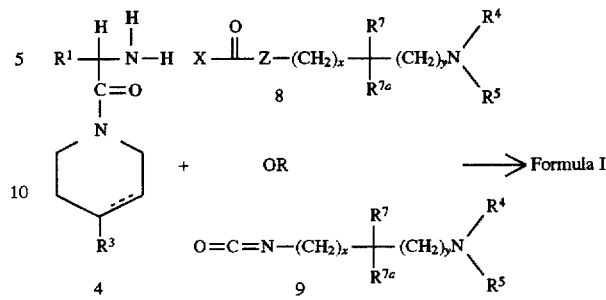

Compounds of formula I, wherein A is Z-(CH$_2$)$_x$-C(R$^7$)(R$^{7a}$)-(CH$_2$)y and Z is N-R$^2$ or 0 can be prepared as shown in Scheme 5 by reacting 4 with reagent 8, wherein X is an appropriate leaving group such as Cl, Br, I, or imidazole. Alternatively, 4 can be reacted with an isocyanate of formula 9 in an inert solvent such as 1,2-dichloroethane which results in a compound of formula I where Z is NH.

The compounds of general formula I of the present invention can also be prepared in a convergent manner as described in reaction schemes 6, 7 and 8.

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other methods includes the reaction of a protected amino acid with a diazoalkane and removal of the protecting group L.

SCHEME 6

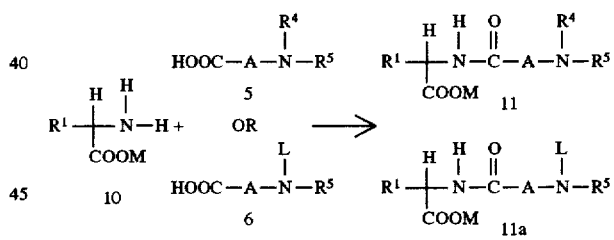

Intermediates of formula 11 or 11a, can be prepared as shown in Scheme 6 by coupling of amino acid esters 10 to amino acids of formula 5 or 6. When a urea linkage is present in 1 1 or 11a, it can be introduced as illustrated in Scheme 5.

SCHEME 7

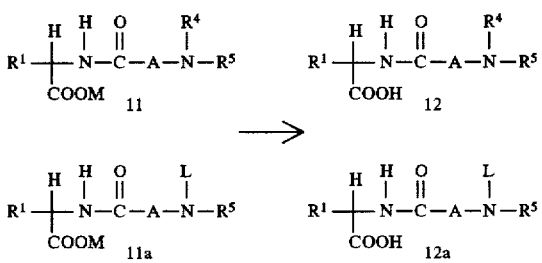

Conversion of the ester 11 or 11a to intermediate acids 12 or 12a can be achieved by a number of methods known in the art as described in Scheme 7. For example, methyl and ethyl esters can be hydrolyzed with lithium hydroxide in a protic solvent like aqueous methanol. In addition, removal of benzyl group can be accomplished by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see *J. Org. Chem.*, 42, 587 (1982)).

FIG. 1

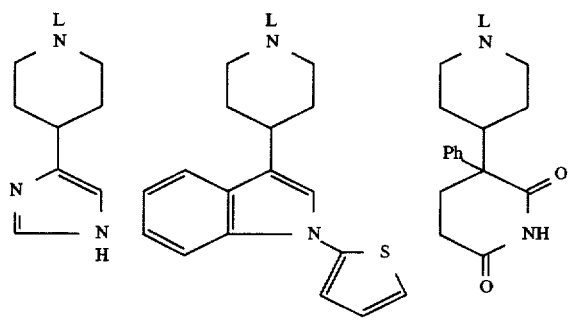

SCHEME 8

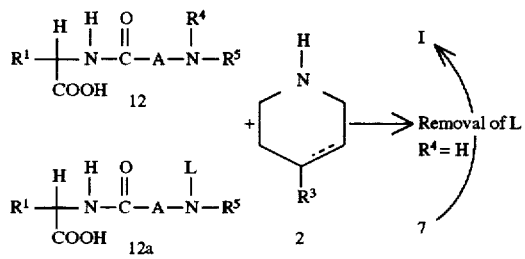

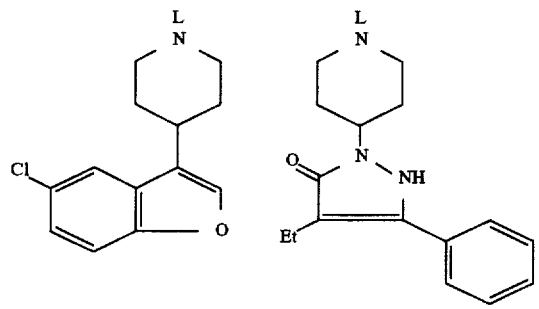

Acid 12 or 12a can then be elaborated to I or compound 7 as described in Scheme 8. Coupling of piperidines of formula 2 to acids of formula 12 or 12a, wherein L is a suitable protecting group, is conveniently carried out under the standard peptide coupling reaction conditions. Transformation of 7 to I is achieved by removal of the protecting group L. When $R^4$ and/or $R^5$ is H, substituted alkyl groups may be optionally added to the nitrogen atom as described in Scheme 4.

The substituted piperidines are either known compounds or can be prepared by literature procedures. Illustrated here are some, but by no means all the methods available for their preparation.

The 4-substituted piperidines depicted in FIGS. 1 and 2, which may be optionally unsaturated in the piperidine ring and/or substituted by $R^8$, and wherein L is an hydrogen, an alkyl, or a BOC or CBZ group, are known in the literature. The piperidines shown in FIGS. 1 and 2 wherein L=H can be elaborated to the instant compounds of Formula I by utilizing chemistry detailed in Schemes 1–8. The piperidines shown in FIGS. 1 and 2 wherein L is an alkyl group can be dealkylated by a number of methods familiar to those skilled in the art, including the cyanogen bromide protocol detailed by H. Ong et al. in *J. Med. Chem.*, 23, 981–986 (1983) and the ACE-Cl method as described in R. Olofson et al. *J. Org. Chem.*, 23, 2795 (1984). The piperidines shown in FIGS. 1 and 2 wherein L is a BOC or CBZ protecting group may be deprotected by well documented methods and elaborated to the instant compounds by using chemistry presented in Schemes 1–8.

FIG. 2

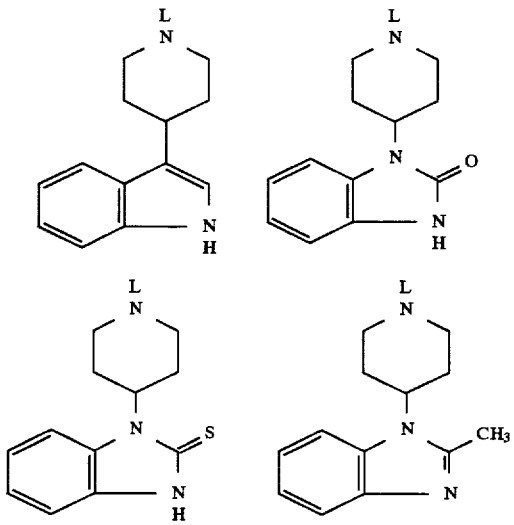

-continued
FIG.2

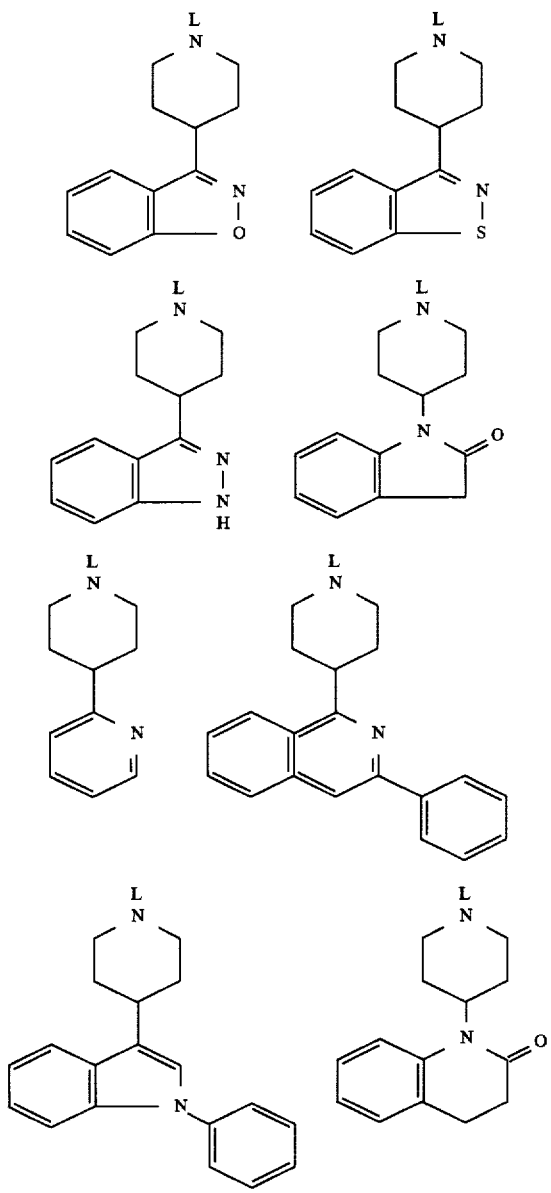

SCHEME 9

As shown in Scheme 9, a general method that may be utilized to prepare a variety of 4-substituted piperidines of formula 2 involves the addition of a metalated heterocycle (for e.g. pyridines, thiophenes, benzothiophenes, quinolines, indoles) to a protected 4-piperidone of formula 13 (L is a methyl or benzyl group) to give a 4-hydroxy compound that can dehydrated to give tetrahydropyridines of formula 14 by methods familiar to those skilled in the art. Removal of L from piperidines of formula 14 may be carried out by a number of methods familiar to those skilled in the art, including the cyanogen bromide protocol detailed by H. Ong et al. in *J. Med. Chem.*, 23, 981–986 (1983) and the ACE-Cl method as described in R. Olofson et al., *J. Org. Chem.*, 23, 2795 (1984). The 4-substituted tetrahydropiperidines obtained by this method can be elaborated to the instant compounds by utilizing chemistry detailed in Schemes 1–8. The piperidines of formula 14 can be hydrogenated by use of platinum or palladium catalysts in a protic solvent like methanol to give piperidines of formula 15 which can also be elaborated to the instant compounds of Formula I.

SCHEME 10

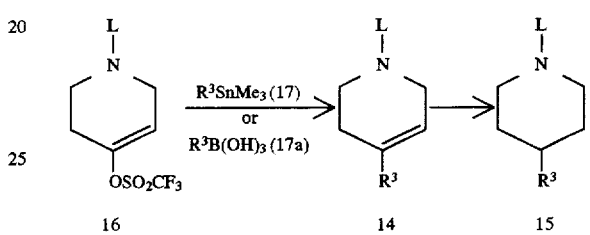

As shown in Scheme 10, other methods may also be utilized to synthesize piperidines of formula 2. For example, cross-coupling of enol triflates of formula 16 (L=protecting group) with heteroarylboronic acids of formula 17a or heteroaryl tin reagents of formula 17, wherein $R^3$ may be any of a number of the heterocycles presented herein, may be accomplished with palladium (II) or palladium (0) catalysts as detailed in the review article by W. J. Scott and J. E. McMurry, *Acc. Chem. Res.*, 21, 47 (1988) to give tetrahydropiperidines 14 (L=protecting group).

Various methods exist for the synthesis of the enol triflate intermediates of formula 16, heteroaryl boronic acids 17a and heteroaryl tin reagents of formula 17 and can be prepared by methods that are familiar to those skilled in the art. Removal of the protecting group L furnishes piperidines of formula 14 (L=H). Hydrogenation of 14 followed by removal of the protection group L gives saturated derivatives 15 (L=H).

SCHEME 11

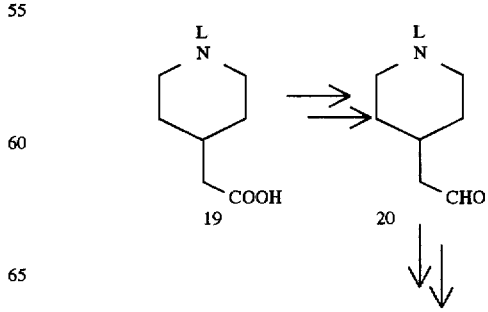

SCHEME 11 -continued

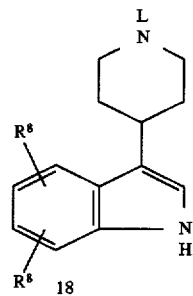

Specifically, piperidines of formula 18, wherein $R^8$ may be any of the substitutents as described herein, may be prepared from the protected piperidine acetic acid compound 19 (L=CBZ) as shown in Scheme 11. Treatment of 19 with either oxalyl chloride or thionyl chloride in an inert solvent like benzene or carbon tetrachloride gives the corresponding acid chloride that is converted to the aldehyde 20 by a Rosemund reduction. Compound 20 is then elaborated to a variety of substituted indoles 18 by utilizing the Fischer indole synthesis (see *J. Chem. Soc. Chem. Commun.*, 563 (1981); *J. Chem. Soc.*, 3175 (1957)). The protecting group L (for e.g. CBZ) can be removed by standard protocols and elaborated to the instant compounds by using chemistry presented in Schemes 1–8.

SCHEME 12

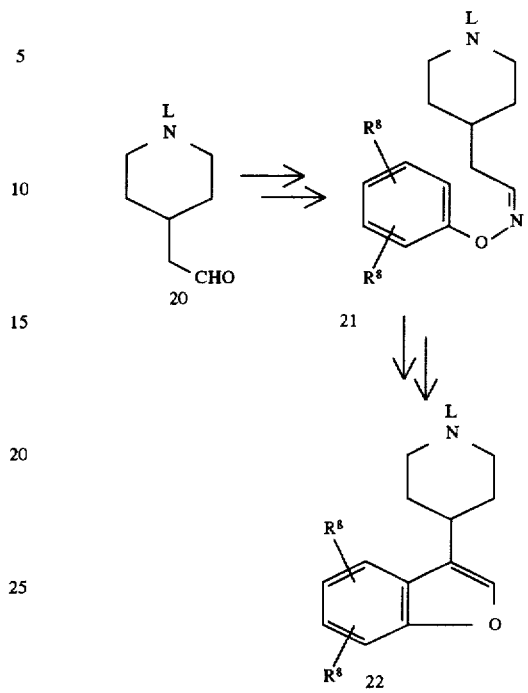

An analogous synthesis of benzofurans of formula 22 from o-aryloximes is exemplified by the transformation of 21 to 22 (see *Tetrahedron Lett.*, 2867 (1967)) as depicted in Scheme 12.

SCHEME 13

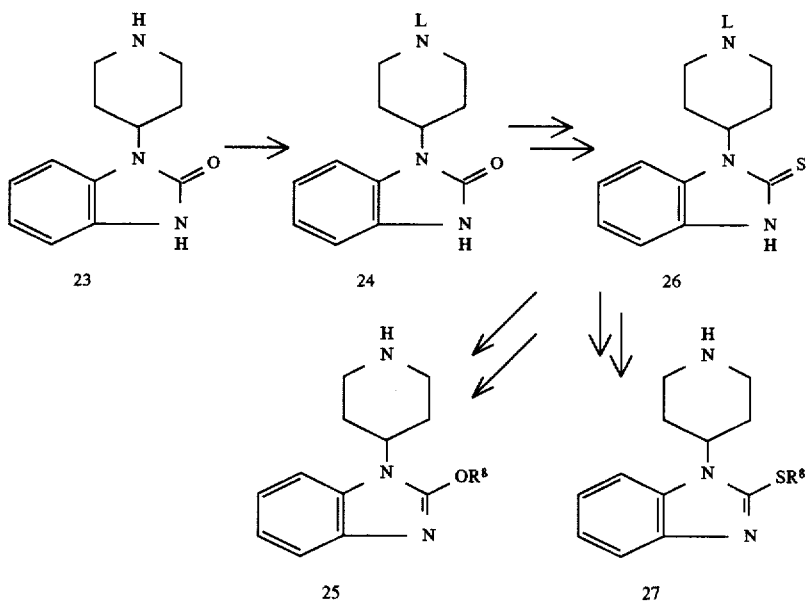

The commercially available compound 4-(2-keto-1-benzimidazolinyl)piperidine 23 may be elaborated to the instant compounds by using chemistry detailed in Schemes 1-8. Furthermore, 23 can serve as an intermediate for the synthesis of instant compounds bearing other heterocyclic substitutents as shown in Scheme 13. Protection of the piperidine with a protecting group L (for e.g. BOC or CBZ) to give 24 can be carried out by methods familiar to those skilled in the art. The piperidine 24 can be treated with a base in an inert solvent like dry tetrahydrofuran or dimethylformamide and the anion can be trapped with electrophiles like alkyl halides and acyl chlorides to give benzimidazoles of formula 25. As shown in Scheme 13, 24 can be treated with Lawesson's reagent in an inert solvent such as toluene to give the piperidine of formula 26 which can be transformed to the instant compounds after removal of the protecting group L. The compound 26 can be elaborated further to provide compounds of formula 27 by treatment of it with base followed by trapping of the thiolate anion thereby generated with alkyl halides.

The compounds of the present invention may also be prepared from a variety of substituted natural and unnatural amino acids of formulas 31. The preparation of many of these acids is described in e.g., U.S. Pat. Nos 5,206,235, 5,283,241, 5,284,841, 5,310,737 and 5,317,017. The preparation of these intermediates in racemic form is accomplished by classical methods familiar to those skilled in the art (Williams, R. M. "Synthesis of Optically Active α-Amino Acids" Pergamon Press: Oxford, 1989; Vol. 7). Several methods exist to resolve (DL)-

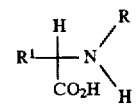

amino acids. One of the common methods is to resolve amino or carboxyl protected intermediates by crystallization of salts derived from optically active acids or amines. Alternatively, the amino group of carboxyl protected intermediates may be coupled to optically active acids by using

SCHEME 14

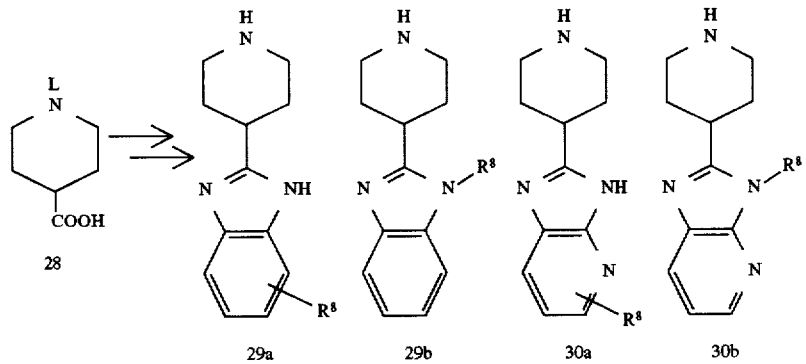

As shown in Scheme 14, other heterocyclic piperidines of formula 2 may be synthesized from a 4-carboxyl piperidine of formula 28 wherein L is a methyl or benzyl group. Compound 28 is reacted with ortho-phenylenediamines or ortho-diamino pyridines in a solvent such as polyphosphoric acid to give benzimidazoles of formula 29a and 29b, and imidazopyridines of formula 30a and 30b. As noted previously, 29a, 29b, 30a and 30b may be elaborated to the instant compounds following removal of the protecting group L.

In additon, acids, acid chlorides, nitriles, and imino-ethers at the 4-position of the a protected piperidine may serve as key intermediates in the preparation of a number of alkyl, phenyl, hydroxy, and amino-substituted heterocycles. Many of the methods are documented in A. Katrizky, Handbook of Heterocycles Pergamon Press, New York, New York (1985) and may be used to synthesize the instant compounds bearing a variety of heterocycles.

When the substituten on the 4-position of the piperidine bears an asymmedric center, the 4-piperidines generated by these synthetic protocols are racemic. These compounds may be resloved by numerous methods including classical resolution of racemates. For example resolution can be achieved by the formation of diastereomeric salts of racemic amines with optically active acids such as D- and L- tartaric acid. The determination of the absolute stereochemistry can be accomplished in a number of ways including X-ray crystallography of a suitable crystalline derivative such as a D- or L- tartaric acid salt.

chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in J. Am. Chem. Soc., 111, 6354–6364 (1989).

When it is desirable to synthesize these intermediates in optically pure form, established methods include: (1) asymmetric electrophilic amination of chiral enolates (J. Am. Chem. Soc., 108, 6394–6395, 6395–6397, and 6397–6399 (1986)), (2) asymmetric nucleophilic amination of optically active carbonyl derivatives, (J. Am. Chem. Soc., 114, 1906 (1992); Tetrahedron Lett., 28, 32 (1987)), (3) diastereoselective alkylation of chiral glycine enolate synthons (J. Am. Chem. Soc., 113, 9276 (1991); J. Org. Chem.,54, 3916 (1989)), (4) diastereoselective nucleophilic addition to a chiral electrophilic glycinate synthon (J. Am. Chem. Soc., 108, 1103 (1986)), (5) asymmetric hydrogenation of prochiral dehydroamino acid derivatives (Asymmetric Synthesis Chiral Catalysis; Morrison, J. D., Ed; Academic Press: Orlando, Fla.; Vol 5 (1985)), and (6) enzymatic syntheses (Angew. Chem. Int. Ed. Engl., 17, 176 (1978)).

SCHEME 15

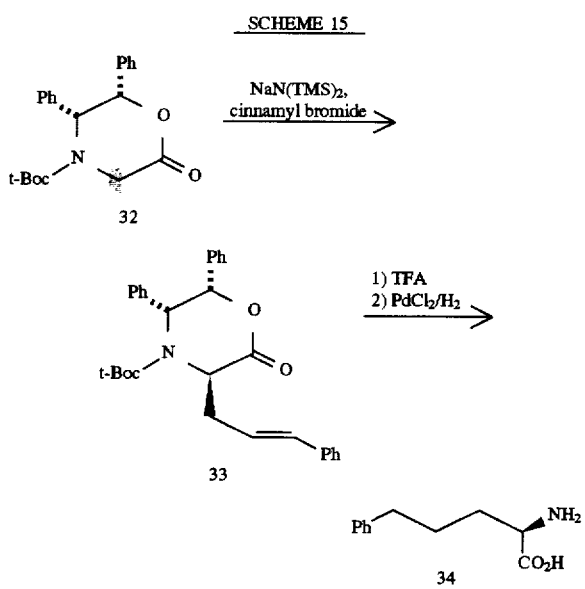

For example, alkylation of the enolate of diphenyloxazinone 32 (*J. Am. Chem. Soc.*, 113, 9276 (1991)) with cinnamyl bromide in the presence of sodium bis(trimethylsilyl) amide proceeds smoothly to afford 33 which is converted into the desired (D)-2-amino-5-phenylpentanoic acid 34 by removing the N-t-butyloxycarbonyl group with trifluoroacetic acid and hydrogenation over a $PdCl_2$ catalyst (Scheme 15).

SCHEME 16

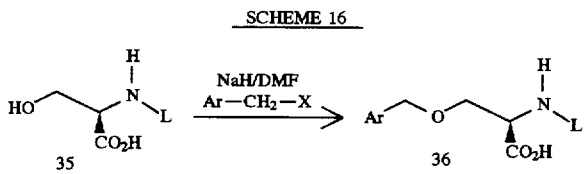

Intermediates of formula 31 which are O-benzyl-(D)-serine derivatives 36 are conveniently prepared from suitably substituted benzyl halides and N-protected-(D)-serine 35. The protecting group L is conveniently a BOC or a CBZ group. Benzylation of 35 can be achieved by a number of methods well known in the literature including deprotonation with two equivalents of sodium hydride in an inert solvent such as DMF followed by treatment with one equivalent of a variety of benzyl halides (*Synthesis*, 36 (1989)) as shown in Scheme 16.

The O-alkyl-(D)-serine derivatives may also be prepared using an alkylation protocol. Other methods that could be utilized to prepare (D)-serine derivatives of formula 36 include the acid catalyzed benzylation of carboxyl protected intermediates derived from 35 with reagents of formula $ArCH_2OC(=NH)CCl_3$ (O. Yonemitsu et al., *Chem. Pharm. Bull.*, 36, 4244 (1988)). Alternatively, alkylation of the chiral glycine enolates (*J. Am. Chem. Soc.*, 113, 9276 (1991); *J. Org. Chem.*, 54, 3916 (1989)) with $ArCH_2OCH_2X$ where X is a leaving group affords 36. In addition D,L-O-aryl(alkyl) serines may be prepared and resolved by methods described above.

It is noted that in some situations the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay described by Smith, et al., *Science*, 260, 1640–1643 (1993) (see text of FIG. 2 therein). In particular, all of the compounds prepared in the following examples had activity as growth hormone secretagogues in the aforementioned assay. Such a result is indicative of the intrinsic activity of the present compounds as growth hormone secretagogues.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, estrogens, β-agonists, theophylline, anabolic steroids, enkephalins, E series prostaglandins, compounds disclosed in U.S. Pat. No. 3,239,345, e.g., zeranol, and compounds disclosed in U.S.

Pat. No. 4,036,979, e.g., sulbenox or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 as described in U.S. Pat. Nos. 4,411,890 and publications WO 89/07110, WO 89/07111 and B-HT920 as well as hexarelin and the newly discovered GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia, treatment of peripheral neuropathies; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; to stimulate thymic development and prevent the age-related decline of thymic function; adjunctive therapy for patients on chronic hemodialysis; treatment of immunosuppressed patients and to enhance antibody response following vaccination; increasing the total lymphocyte count of a human, in particular, increasing the T4/T8-cell ratio in a human with a depressed T4/T8-cell ratio resulting, for example, from physical trauma, such as closed head injury, or from infection, such as bacterial or viral infection, especially infection with the human immunodeficiency virus; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock.

In particular, the instant compounds are useful in the prevention or treatment of a condition selected from the group consisting of: osteoporosis; catabolic illness; immune deficiency, including that in individuals with a depressed $T_4/T_8$ cell ratio; hip fracture; musculoskeletal impairment in the elderly; growth hormone deficiency in adults or in children; obesity; cachexia and protein loss due to chronic illness such as AIDS or cancer; and treating patients recovering from major surgery, wounds or burns, in a patient in need thereof.

It will be known to those skilled in the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N.A.T., Role of Bisphosphonates in Metabolic Bone Diseases, Trends in Endocrinol. Metab., 4, 19–25 (1993). Bisphosphonates with these utilities include alendronate, tiludronate, dimethyl - APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone.

The following examples are provided for the purpose of further illustration only and are not intended to be limitations on the disclosed invention.

INTERMEDIATE 1

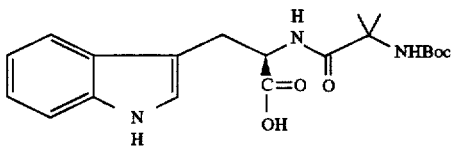

Step A:

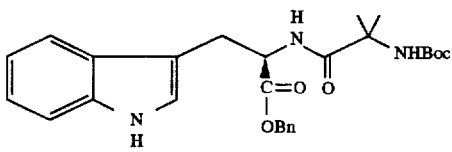

To 5.0 g (16.5 mmole) of the commercially available N-t-BOC-D-tryptophan in 100 mL of chloroform was added 1.80 mL (16.5 mmole) of benzyl alcohol, 0.20 g (1.65 mmole) of 4-N,N-dimethylamino pyridine (DMAP), and 3.20 g of EDC and stirred for 16h. The reaction mixture was poured into 100 mL of water and the organic layer was separated. The aqueous was further extracted with 2×100 mL of chloroform. The combined organic solution was washed with 50 mL of 10% aqueous citric acid, 100 mL of 10% aqueous sodium bicarbonate solution, dried over anhydrous magnesium sulfate, filtered and concentrated to give a thick oil.

To a solution of this oil in 10 mL of dichloromethane was added 20 mL of trifluoroacetic acid and stirred for 1 h. The reaction mixture was concentrated, basified carefully with saturated aqueous sodium bicarbonate solution, and extracted with chloroform (2×100 mL). The combined organic solution were washed with brine (100 mL), dried over potassium carbonate, filtered, and concentrated to give 5.46 g of the amine as a brown oil which was used without purification.

To 5.46 g of the above product in 100 mL of chloroform was added 3.40 g (22.2 mmole) of HOBT, 4.60 g (22.2 mmole) of N-BOC-α-methyl alanine, and 5.32 g (28.0 mmole) of EDC and stirred for 16 h. The reaction mixture was poured into 100 mL of water and the organic layer was separated. The aqueous was further extracted with 2×100 mL of chloroform. The combined organic solution were washed with 50 mL of 10% aqueous citric acid, 100 mL of 10% aqueous sodium bicarbonate solution, dried over anhydrous magnesium sulfate, filtered and concentrated to give 6.94 g of the product as a thick oil. Flash chromatography (200 g SiO$_2$; hexane-ethyl acetate as eluent) gave 4.75 g of the desired material as a colorless foam.

$^1$H NMR (CDCl$_3$, 200 MHz) d 8.48 (bs, 1H), 7.54 (bd, 1H), 7.38–7.23 (m, 3H), 7.19 (bd, 2H), 7.15–7.00 (m, 1H), 6.90 (d, 1H), 6.86 (d, 1H), 5.06 (bs, 2H), 4.95 (ddd, 1H), 3.30 (2dd, 2H), 1.40 (s, 15H)

Step B:

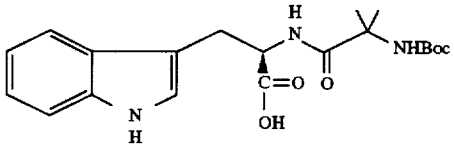

To a solution of 4.75 g of the material from Step A in 100 mL of ethanol was added 1.0 g of 10% Pd/C and stirred at RT under a H$_2$ balloon for 18 h. The catalyst was filtered off through a pad of celite and washed with ethyl acetate. The filtrate was concentrated to give 2.96 g of the acid as a colorless foam.

$^1$H NMR (CDCl$_3$, 200 MHz) d 8.60 (bs, 1H), 7.55 (d, 1H), 7.26–6.90 (m, 3H), 6.88 (bd, 1H), 4.80 (m, 1H), 3.32 (2dd, 2H), 1.37 (s, 3H), 1.35 (s, 12H)

INTERMEDIATE 2

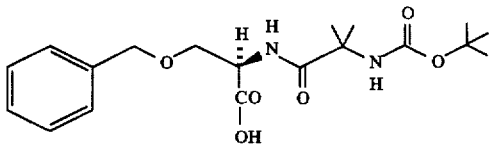

Step A:

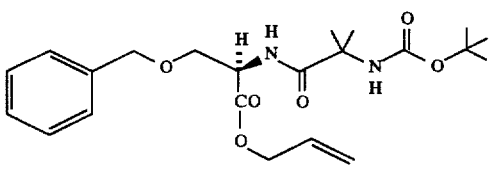

Prepared from N-tBOC-O-benzyl-D-serine and allyl alcohol by the procedure described in Intermediate 1, Step A and subsequent coupling to N-BOC-α-methylalanine to give the desired compound.

$^1$H NMR (400 MHz, CDCl$_3$) d 7.25 (s, 5H), 5.8 (m, 1H), 5.2 (dd, 2H), 5.0 (bs, 1H), 4.7 (m, 1H), 4.6 (m, 2H), 4.4 (dd, 2H), 3.9 (dd, 1H), 3.6 (dd, 1H), 1.45 (d, 6H), 1.39 (s, 9H).

Step B:

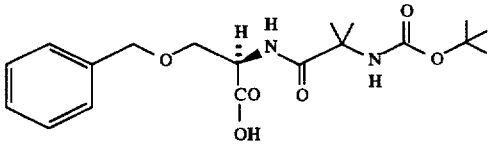

To a stirred solution of the crude intermediate obtained in Step A (6.7 g, 15.9 mmol), tetrakis (triphenylphosphine)-palladium (1.8 g, 0.1 eq) and, triphenyl phosphine (1.25 g, 0.3 eq) was added a solution 10 of potassium-2-ethyl hexanoate (35 mL, 0.5M solution in EtOAc). The reaction mixture was stirred at room temperature under nitrogen atmosphere for 1 h and then diluted with ether (100 mL) and poured into ice-water. The organic layer was seperated and the aqueous fraction was acidified with citric acid (20%), then extracted with EtOAc. The EtOAc extracts were washed with brine, dried over magnesium sulfate, filtered and evaporated to give the title compound as a solid.

$^1$H NMR (400 Hz, CD$_3$OD) d 7.3 (s, 5H), 4.7 (m, 1H), 4.5 (s, 2H), 4.0 (m, 1H), 3.6 (m, 1H), 1.4 (d, 6H), 1.3 (s, 9H).

INTERMEDIATE 3

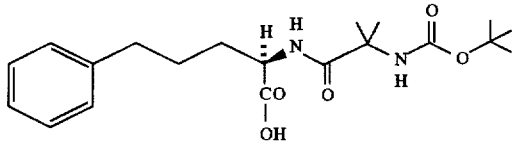

This intermediate was synthesized as described in Step A and B of Intermediate 1, but (2R)-N-t-BOC-5-phenylpentanoic acid (H. K. Chenault et al., *J. Am. Chem. Soc.*, 111, 6354–6364 (1989)) was used in place of N-t-BOC-(D)-Tryptophan.

$^1$H NMR (CDCl$_3$, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

EXAMPLE 1

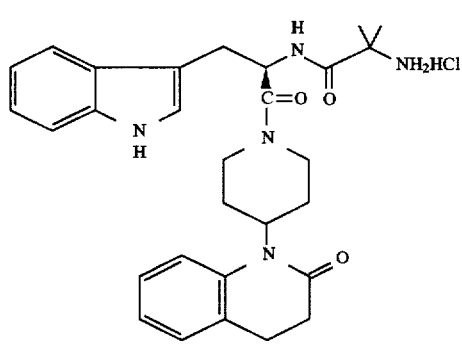

Step A:

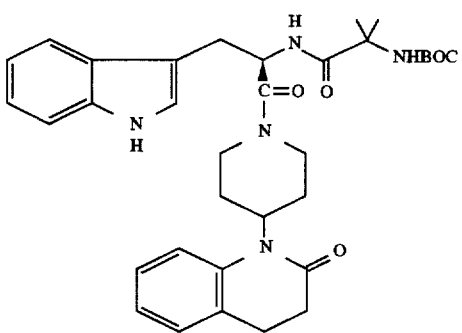

To a solution of the hydrochloride salt of 1-(piperidin-4-yl)-3,4-dihydro-2(1H)-quinolinone (16.7 mg; prepared by the method of Ogawa et al., *J. Med. Chem.*, 36, 2011–2017 (1993)), Intermediate 1 (1 eq.), HOBT (1 eq.), and N-methyl morpholine (1 eq.) in dichloromethane at 0° C. was added EDC (1.5 eq.). The reaction mixture was stirred at 0° C. overnight. The solution was washed with saturated sodium chloride, dried over anhydrous magnesium sulfate; then filtered and concentrated. Purification by silica gel flash chromatography eluting with 80–100% ethyl acetate in hexane provided the desired compound (20.4 mg).

FAB-MS calc. for C$_{34}$H$_{43}$N$_5$O$_5$: 601; Found 602 (M+H)

Step B:

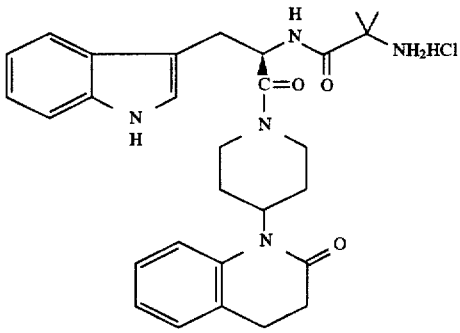

To a stirred solution of the intermediate from the previous step (16.4 mg) in methanol (1 mL) was added concentrated hydrochloric acid (1 mL) and the resulting mixture was stirred at room temperature for two hours. Toluene (5 mL) was added and the resulting mixture was evaporated in vacuo to dryness to yield a white foam (15 mg).

FAB-MS calc. for C$_{29}$H$_{35}$N$_5$O$_3$: 501; Found 502 (M+H)

EXAMPLE 2

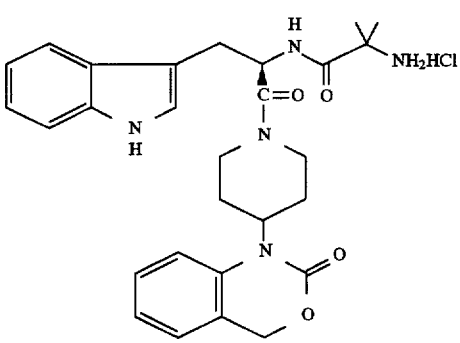

Step 2 A: N-t-butyloxycarbonyl-4-1piperidinone

To a stirred, 0° C. solution of 4-piperidinone hydrochloride hydrate (50 g; 0.33 mol) in DMF (500 mL) was added di-t-butyl dicarbonate (64 g; 0.29 mol) followed by a dropwise addition of DIEA (63 mL; 0.36 mol). After the addition of DIEA was complete, the reaction was allowed to gradually warm to ambient temperature over 4 h and stirring was continued for 20 h. The DMF was removed under reduced pressure and the residue was dissolved in EtOAc (1000 mL) and washed with 5% aqueous citric acid (2×500 mL), water (250 mL), and saturated aqueous NaHCO$_3$ (500 mL). The EtOAc layer was dried (Na$_2$SO$_4$), filtered, and the EtOAc was removed under reduced pressure. The residue was boiled in ether (ca. 250 mL) until the solid had dissolved. Cooling gave N-t-butyloxycarbonyl-4-piperidinone as white crystals (47 g; 80% yield).

Step B: 1-t-Butyloxycarbonyl-4-((2-hydroxymethyl)phenylamino)piperidine

N-t-butyloxycarbonyl-4-piperidinone (20 g, 0.10 mol) from Step A, 2-aminobenzyl alcohol (13 g, 0.11 mol), and acetic acid (14 mL, 0.22 mol) were dissolved in dry toluene (500 mL). The solution was refluxed under inert atmosphere with azeotropic removal of water for 16 h. The solution was cooled to ambient temperature and to it was added NaBH$_3$CN (14 g, 0.22 mol) and dry THF (200 mL). The reaction was stirred at ambient temperature for 24 h. The reaction was concentrated under reduced pressure and the residue was dissolved in EtOAc (750 mL). The EtOAc layer was washed with saturated aqueous NaHCO₃ (4×500 mL) and brine (250 mL). The EtOAc layer was dried (MgSO₄), filtered, and the solvent was removed under reduced pressure. The residue was purified by pressurized silica gel column chromatography, using a gradient elution of 15–30% EtOAc-hexane. 1-t-Butyloxycarbonyl-4-((2-hydroxymethyl)phenylamino)piperidine was obtained as a gum (24 g, 78% yield).

Step C: 1-((1-t-Butyloxycarbonyl)piperidin-4-yl)-1,2-dihydro-4(H)-3,1-benzoxazin-2-one 1-t-Butyloxycarbonyl-4-((2-hydroxymethyl) phenylamino)piperidine (24 g, 78 mmol) from Step B was dissolved in dry THF (250 mL) and cooled to 0° C. To the solution was added DIEA (41 mL, 0.24 mol) and triphosgene (8.54 g, 28.8 mmol). The reaction was stirred at 0° C. for 1 h, and then at ambient temperature for 72 h. Ether (250 mL) was added, the mixture was cooled to 0° C. for 3 h and then filtered to remove the hydrochloride salt of DIEA. The filtrate solvents were removed under reduced pressure and the residue was dissolved in EtOAc (750 mL). The EtOAc solution was washed with 5% aqueous citric acid (2×500 mL), water (250 mL), and saturated aqueous NaHCO₃ (2×500 mL). The EtOAc layer was dried (MgSO₄), filtered, and the solvent was removed under reduced pressure. The residue was boiled in ether (ca. 200 mL) until the solid had dissolved. Cooling overnight gave 1-((1-t-butyloxycarbonyl)piperidin-4-yl)-1,2-dihydro-4(H)-3,1-benzoxazin-2-one as off-white crystals (19 g; 75% yield).

Step D: 1-(4-piperidinyl)-1,2-dihydro-4(H)-3,1-benzoxazin-2-one hydrochloride salt A stirred solution of 1-((1-t-butyloxycarbonyl)-piperidin-4-yl)-1,2-dihydro-4(H)-3,1-benzoxazin-2-one (19 g, 57 mmol) from Step C in EtOAc (500 mL) was cooled to 0° C. HCl gas was bubbled through the solution for 30 min. Stirring was continued at 0° C. for 1 h, during which time a precipitate had formed, and then at ambient temperature for 1 h. The stirred suspension was cooled to 0° C. and cold ether (250 mL) was added. After 1 h at 0° C., the solid was collected by filtration. The solid was dried under reduced pressure for 18 h, giving the hydrochloride salt of 1-(4-piperidinyl)-1,2-dihydro-4(H)-3,1-benzoxazin-2-one as an off-white solid (14 g, 91% yield).

Step E:

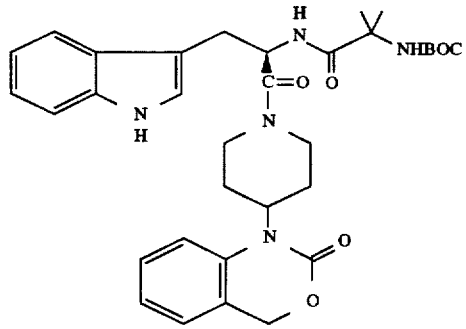

To a solution of the hydrochloride salt of 1-(4-piperidinyl)-1,2-dihydro-4(H)-3,1-benzoxazin-2-one prepared in the previous step( 25 mg), Intermediate 1 (1 eq.), HOBT (1 eq.), and N-methyl morpholine (1 eq.) in dichloromethane at 0° C. was added EDC (1.5 eq.). The reaction mixture was stirred at 0° C. overnight. The solution was washed with saturated sodium chloride, dried over anhydrous magnesium sulfate; then filtered and concentrated. Purification by silica gel flash chromatography eluting with 60–80% ethyl acetate in hexane provided the desired compound (27.8 mg).

FAB-MS calc. for C₃₃H₄₁N₅O₆: 603; Found 604 (M+H)

Step F:

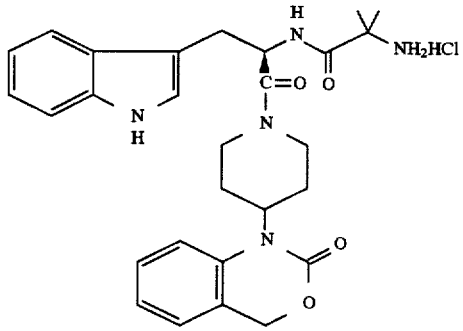

To a stirred solution of the intermediate from the previous step (27 mg) in methanol (1 mL) was added concentrated hydrochloric acid (1 mL) and the resulting mixture was stirred at room temperature for two hours. Toluene (5 mL) was added and the resulting mixture was evaporated in vacuo to dryness to yield a white foam (20 mg).

FAB-MS calc. for C₂₈H₃₃N₅O₄: 503; Found 504 (M+H)

EXAMPLE 3

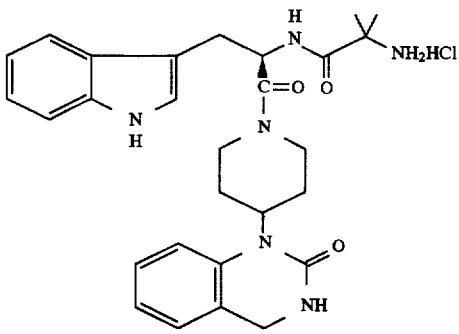

Step A: 2-(t-Butyloxycarbonylaminomethyl)aniline

To a solution of 2-(aminomethyl)aniline (4.86 g, 39.8 mmol) in DMF (125 mL) was added a solution of di-t-butyldicarbonate (7.38 g, 0.339 mmol) in DMF (60 mL) dropwise over a period of 1 hour. After being stirred for 18 h at ambient temperature, the solvent was removed under reduced pressure. The residue was dissolved in EtOAc (100 mL) and washed with 5% aqueous citric acid (2×50 mL) and water (50 mL). The EtOAc layer was dried (Na₂SO₄), filtered, and the solvent was removed under reduced pressure to give 2-(t-butyloxycarbonyl-aminomethyl)aniline as an oil (75% yield).

Step B: 1-Benzyl-4-((2-t-butloxycarbonylaminomethyl) phenylamino)piperidine

To a stirred solution of 2-(t-butyloxycarbonylaminomethyl)aniline (2.18 g, 9.82 mmol) from Step A in dry toluene (100 mL) was added N-benzyl-4-piperidinone (2.04 g, 10.8 mmol) and crushed, activated 4 angstrom molecular sieves (5 g). The mixture was stirred at ambient temperature for 72 h. The sieves were removed by filtration and the solvent was removed under reduced pressure. The residue was dissolved in MeOH (100 mL) and acetic acid (1 mL) and NaCNBH₃ (2.25 g, 35.7 mmol) were added. After being stirred for 16 h at ambient temperature, 10 mL of saturated NaHCO₃ were added and the reaction was concentrated under reduced pressure. EtOAc (150 mL)

was added, and the solution was washed with saturated aqueous NaHCO₃ (3×50 mL). The EtOAc layer was dried (MgSO₄), filtered, and the solvent was removed under reduced pressure to give 1-benzyl-4-((2-t-butlyoxycarbonylaminomethyl)phenylamino)piperidine as an oil (90% yield).

Step C: 1-Benzyl-4-((2-aminomethyl)phenylamino) piperidine

To a solution of 1-benzyl-4-((2-t-butlyoxycarbonylaminomethyl)phenylamino)piperidine (3.49 g, 8.83 mmol) from Step 2 in CHCl₃ (5 mL) was added TFA (5 mL). After 2 h, the solvents were removed under reduced pressure. The residue was dissolved in CHCl₃ (100 mL) and washed with saturated aqueous NaHCO₃ (75 mL). The CHCl₃ layer was concentrated under reduced pressure and the residue was purified by pressurized silica gel column chromatography using 96:4:0.4 CHCl₃:MeOH:NH₄OH as eluant. 1-Benzyl-4-((2-aminomethyl)phenylamino) piperidine was obtained as an oil (65% yield).

Step D: 1-(1-Benzyl-4-piperidinyl)-3,4-dihydroquinazolin-2 (1H)-one

To a solution of 1-benzyl-4-((2-aminomethyl) phenylamino)piperidine (1.74 g, 5.90 mmol) from Step C in dry DMF (50 mL) was added 4-nitrophenyl chloroformate (1.25 g, 6.20 mmol) and DIEA (3.08 mL, 17.7 mmol). After the reaction had been stirred at ambient temperature for 24 h, the solvent was removed under reduced pressure. The residue was dissolved in DCM (100 mL) and washed with saturated aqueous NaHCO₃ (4×50 mL), dried (MgSO₄), and filtered. The solution was concetrated and the precipitate which formed was collected by filtration to give 1-(1-benzyl-4-piperidinyl)-3,4-dihydroquinazolin-2(1H)-one as a white solid (50% yield).

Step E: 1-(4-Piperidinyl)-3,4-dihydroquinazolin-2(1H)-one

To a solution of 1-(1-benzyl-4-piperidinyl)-3,4-dihydroquinazolin-2(H)-one (947 mg, 2.95 mmol) from Step D in dry dichloroethane (20 mL) was added 1-chloroethyl chloroformate (0.35 mL, 3.2 mmol). The reaction was refluxed for 3 h. The solvent was rmoved under reduced pressure and the residue was dissolved in MeOH (50 mL) and the solution was refluxed for 1 h. The reaction was cooled to ambient temperature, conc. NH₄OH (1 mL) was added, and the solvent was remove d under reduced pressure. The residue was purified by pressurized silica gel column chromatography using 90:10:1 CHCl₃3: MeOH: NH₄OH as eluant. 1-(4-Piperidinyl)-3,4-dihydroquinazolin-2(1H)-one was obtained as an oil (48% yield).

Step F:

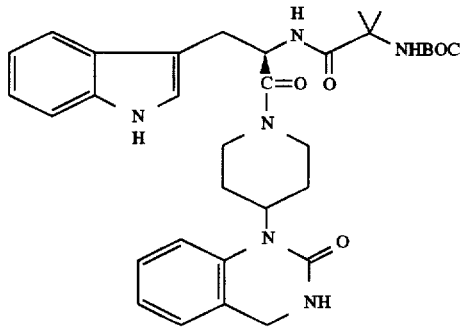

To a solution of the hydrochloride salt of 1-(4-piperidinyl)-3,4-dihydroquinazolin-2(1H)-one from Step E (21.3 mg), Intermediate 1 (1 eq.), HOBT (1 eq.), and N-m ethyl morpholine (1 eq.) in dichloromethane at 0° C. was added EDC (1.5 eq.). The reaction mixture was stirred at 0° C.

overnight. The solution was washed with saturated sodium chloride, dried over an hydrous magnesium sulfate; then filtered and concentrated. Purification by silica gel flash chromatography eluting with 0–5% methanol in ethyl acetate provided the desired compound (26.4 mg).

FAB-MS calc. for $C_{33}H_{42}N_6O_5$: 602; Found 603 (M+H)

Step G:

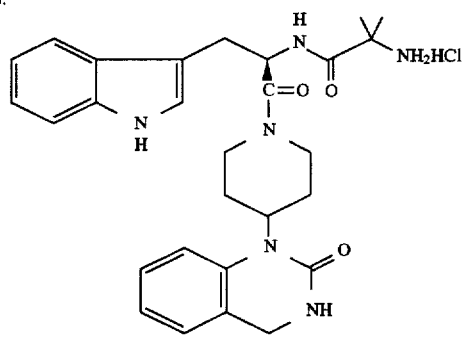

To a stirred solution of the intermediate from the previous step (22 mg) in methanol (1 mL) was added concentrated hydrochloric acid (1 mL) and the resulting mixture was stirred at room temperature for two hours. Toluene (5 mL) was added and the resulting mixture was evaporated in vacuo to dryness to yield a white foam (18 mg).

FAB-MS calc. for $C_{28}H_{34}N_6O_3$: 502; Found 503 (M+H)

EXAMPLE 4

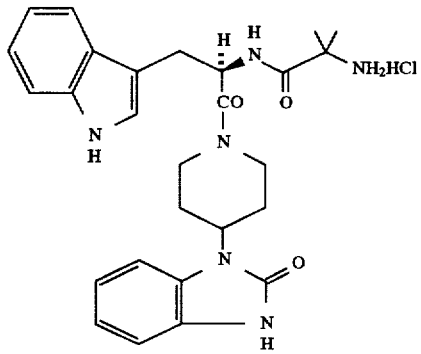

Step A:

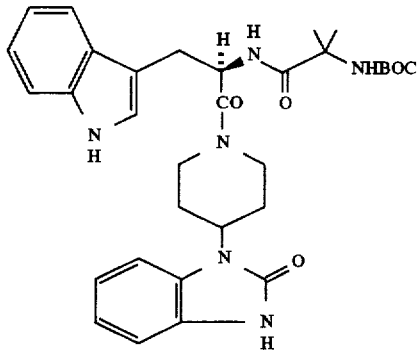

To a stirred solution of 0.068 g of the commercially available 4-(2-keto-1-benzimidazolinyl)piperidine in 10 mL of dichloromethane was added at room temperature 0.138g of Intermediate 1, 0.050 g of HOBT and 0.150 g of EDC and stirred for 18 h. The reaction mixture was washed with 10 mL of 0.50N aqueous HCl, 10 mL of saturated aqueous NaHCO₃, dried over anhydrous MgSO₄ and concentrated to give a residue that was chromatographed on 20 g of silica gel. Elution with CH₂Cl₂-acetone (2:1) gave the desired material as a foam.

¹H NMR (CDCl₃, 400 MHz; mixture of rotamers) 9.82 and 9.75 (2 singlets, 1H), 8.55 and 8.44 (2 singlets, 1H), 7.82 and 7.59 (2 doublets, 1H), 7.38 (2 doublets, 1H), 7.26 (2 doublets, 1H), 7.20-6.90 (m, 6¹/²H), 6.62 (d, 1/2H), 5.40–5.30 and 5.30–5.20 (2 multiplets, 1H), 5.18 and 5.11 (2 singlets, 1H), 4.70 (dd, 1H), 4.30 and 4.10 (2 dt, 1H), 3.68 (bt, 1H), 3.30–3.05 (m, 2H), 2.83 and 2.50 (2 triplets, 1H), 2.35–1.90 (m, 3H), 1.70 (bt, 1H), 1.52, 1.50, 1.49 (3 singlets, 6H), 1.42 (s, 9H), 1.15 and 0.90 (2 multiplets, 1 H).

Step B:

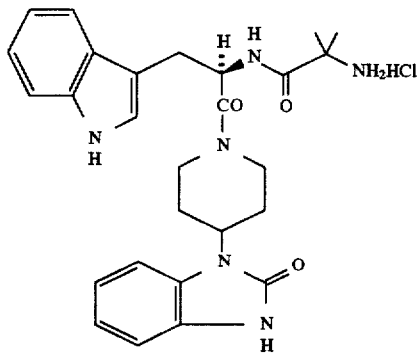

A solution of 0.051 g of the compound prepared in Step A in 2 mL of ethyl acetate was treated with HCl gas for 30 seconds. Ether was added and the precipitate was filtered under an nirtogen atmosphere to give 0.033 g of the title compound as a white solid.

¹H NMR (CD₃OD, 400 MHz; mixture of rotamers) 7.80 and 7.55 (2 doublets, 1H), 7.40–6.90 (m, 7¹/²H), 6.62 (d, ½H), 5.35–5.10 (multiplets, 1H), 4.70 (dd, 1H), 4.30 and 4.10 (2 broad doublets, 1H), 3.65 (bt, 1H), 3.30–3.05 (m, 2H), 2.80 and 2.50 (2 triplets, 1H), 2.35–1.90 (m, 3H), 1.70 (bt, 1H), 1.55, 1.53, 1.50 (3 singlets, 6H), 1.15 and 0.90 (2 multilpets, 1H).

EXAMPLE 5

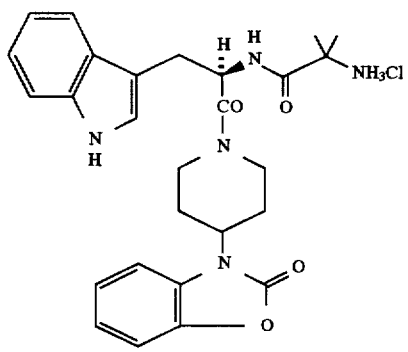

The title compound was prepared in an analogous manner to the compound synthesized in Example 4 but 4-(2-keto-1-benzoxazinyl)piperidine was used in place of 4-(2-keto-1-benzimidazolinyl)piperidine.

¹H NMR (CD₃OD, 400 MHz; mixture of rotamers) 7.83 and 7.53 (2 doublets, 1H), 7.35–7.00 (m, 7¹/²H), 6.60 (d, ½H), 5.35–5.10 ( multiplets, 1H), 4.72 and 4.68 (2 bd, 1H), 4.32 and 4.27 (2 broad doublets, 1H), 4.10 and 3.87 (bt, 1H), 3.30–3.05 (m, 2H), 2.70 and 2.40 (2 triplets, 1H), 2.22–1.60 (m, 3H), 1.70 (bt, 1H), 1.52 and 1.50 (2 singlets, 6H), 1.15 and 0.90 (2 multilpets, 1H).

EXAMPLE 6

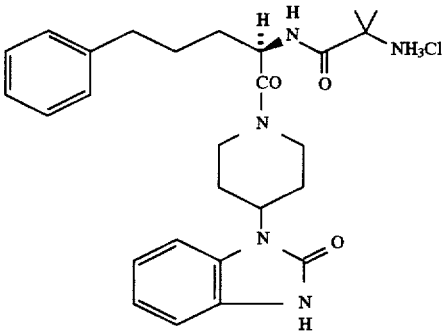

Step A:

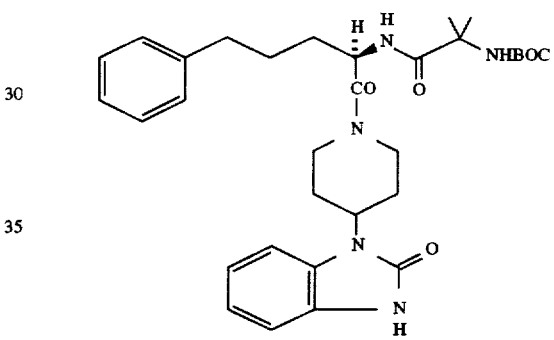

To a solution of 0.140 g of 4-(2-keto-1-benzimidazolinyl) piperidine in 5 mL of dichloromethane was added 0.168 g of (2R)-N-tBOC-5-phenylpentanoic acid, 0.110 g of HOBT and 0.140 g of EDC and stirred at room temperature overnight. The reaction mixture was diluted with 10 mL of CH₂Cl₂ and washed with 10 mL of 0.50N HCl, 10 mL of 10% aqueous Na₂CO₃, dried over MgSO₄ and concentrated. The residue was dissolved 2mL of CH₂Cl₂ and treated with 1 mL of TFA for 30 min. The reaction mixture was evaporated to dryness, the residue was basified with 10% aqueous Na₂CO₃ solution and extracted with CH₂Cl₂. The combined organics were washed with brine, dried over anhydrous K₂CO₃, filtered and dried to give a residue that coupled with 0.140 g of N-tBOC-a-methylalanine in the presence of 0.120 g of HOBT and 0.150 g of EDC. Work-up as described above gave a crude product that was purified by flash chromatography (20 g silica gel) with hexane-acetone (2:1 to 1:1) as the eluent to give 0.149 g of the desired material.

¹H NMR (CDCl₃, 400 MHz; mixture of rotamers) 8.85 and 8.73 (2 singlets, 1H), 7.30–6.90 (m, 9H), 5.03–4.90 (m, 2H), 4.77 (bd, 1H), 4.60–4.40 (m, 1H), 4.05 and 3.96 (2 bd, 1H), 3.15 and 3.06 (2t, 1H), 2.70–2.55 (m, 3H), 2.45–2.00 (m, 2H), 1.93–1.60 (m, 6H), 1.60, 1.50, 1.48, 1.46 (4 singlets, 6H), 1.40 (s, 9H).

Step B:

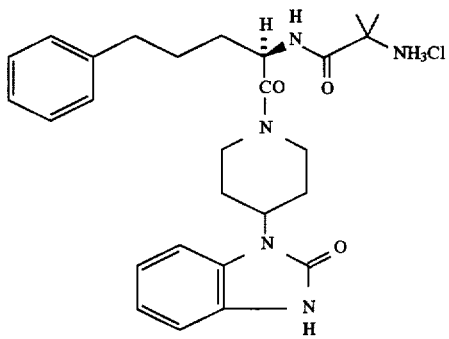

The compound prepared in Step A was deprotected by the HCl/EtOAc protocol as described in Example 4 to give the title compound as a white solid.

$^1$H NMR (CD$_3$OD, 400 MHz; mixture of rotamers) 7.30–6.90 (m, 9H), 5.03–5.00 (m, 1H), 4.77 (bd, 1H), 4.60–4.40 (m, 1H), 4.05 and 3.96 (2 bd, 1H), 3.15 and 3.06 (2t, 1H), 2.70–2.55 (m, 3H), 2.45–2.00 (m, 2H), 1.93–1.60 (m, 6H), 1.60, 1.50, 1.48, 1.46 (4 singlets, 6H).

EXAMPLE 7

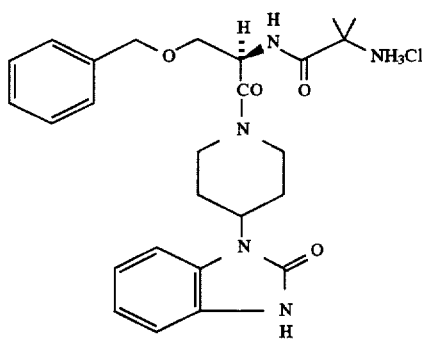

The title compound was prepared in an analogous manner to Example 4 but Intermediate 2 was used in place of Intermediate 1.

EXAMPLE 8

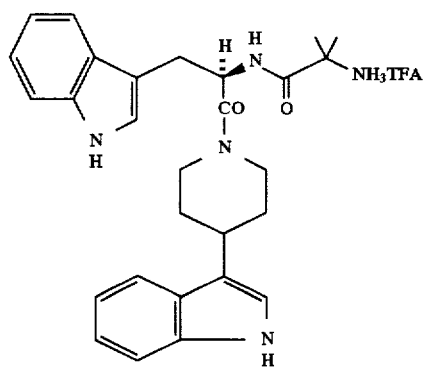

To a solution of 0.001 g of 4-(3-(1H-indolyl))piperidine in 1.5mL of CH$_2$Cl$_2$ was added 0.003 g of Intermediate 1, 0.002 g of HOBT, and 0.003 g of EDC and stirred at room temperature for 18 h. The reaction mixture was diluted with 10 mL of CH$_2$C$_{l2}$ and washed with 5 mL of 0.50N HCl, 5 mL of saturated aqueous NaHCO$_3$, dried over MgSO$_4$, filtered and concentrated to give a residue that was purified by flash chromatography (5 g silica gel; hexane-acetone (2:1) as eluent) to give 0.0036 g of the coupled product. This material was dissolved in 0.50 mL of CH$_2$Cl$_2$ and treated with 0.50 mL of TFA for 30 min and the reaction mixture was evaporated to dryness. The residue was triturated with ether to give 0.0021 g of the title compound as a solid.

EXAMPLE 9

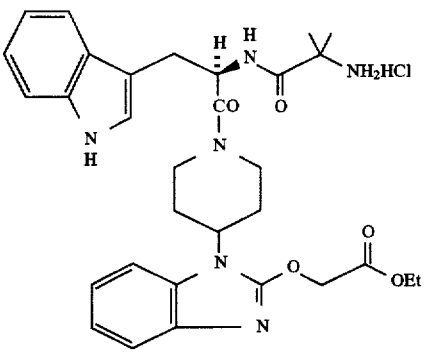

Step A:

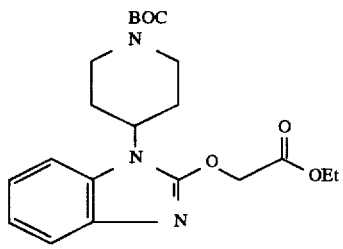

To 2.40g of 4-(2-ketobenzimidazolinyl)piperidine in 50 mL of CH$_2$Cl$_2$ was added at 0° C. 1.70 mL of triethylamine and 2.40 g of di-t-butylcarbonate and stirred at room temperature for 2 h. The reaction mixture was washed with 0.50N HCl (25 mL), 25 mL of saturated aqueous NaHCO$_3$ solution, dried over MgSO$_4$ and concentrated to give the Nt-BOC protected piperidine as a pale yellow solid.

To a solution of the above intermediate in 50 mL of dry THF at −78° C. was added 3.80 mL of a 1M solution of sodium bistrimethylsilylamide in tetrahydrofuran and stirred for 30 min. To the reaction mixture was now added 3.80 mmol of ethyl bromoacetate and allowed to warm-up to room temperature and stirred for 2 h. The reaction mixture was quenched with 20 mL of saturated aqueous ammonium chloride solution and extracted with ethyl acetate (3×25 mL). The combined organics were washed with brine (50 mL), dried over MgSO$_4$ and concentrated to give the desired material.

$^1$H NMR (CDCl$_3$, 400 MHz) 7.10 (dd, 1H), 7.04 (dd, 1H), 6.84 (dd, 1H), 4.58 (s, 2H), 4.50–4.22 (m, 2H), 4.20 (2 q+1m, 3H), 2.90–2.75 (m, 2H), 2.28 (dq, 2H), 1.86–1.76 (m, 2H), 1.46 (s, 9H), 1.25 (2t, 3H).

Step B:

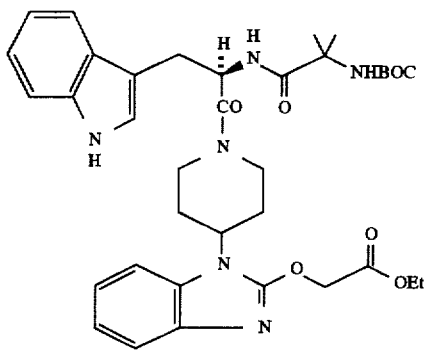

To a solution of 0.87 g of the intermediate prepared in Step A in 3 mL of $CH_2Cl_2$ was added 1 mL of TFA and stirred at RT for 30 min. The reaction mixture was evaporated to dryness, basified with 10% aqueous sodium carbonate solution, and extracted with $CH_2Cl_2$. The combined organics were dried over $K_2CO_3$, filtered and concentrated to give the piperidine that was elaborated to the desired compound with coupling it with Intermediate 1 under the EDC/HOBT conditions as described previously.

$^1$H NMR ($CDCl_3$, 400 MHz; mixture of rotamers) 8.62 and 8.50 (2 singlets, 1H), 7.83 and 7.58 (2 doublets, 1H), 7.35–6.60 (m, 8H), 5.37–5.15 (m, 1H), 5.09 and 5.00 (2 bs, 1H), 4.73 and 4.65 (2bd, 1H), 4.60–4.50 (m, 2H), 4.42–4.00 (m, 3H), 3.63 and 3.52 (2 bd, 1H), 3.30–3.05 (m, 2H), 2.80–1.95 (m, 4H), 1.83–1.60 (m, 1H), 1.51, 1.50 and 1.48 (3s, 6H), 1.41 (s, 9H), 1.23 (2q, 3H), 1.05 and 1.66 (m, 1H).

Step C:

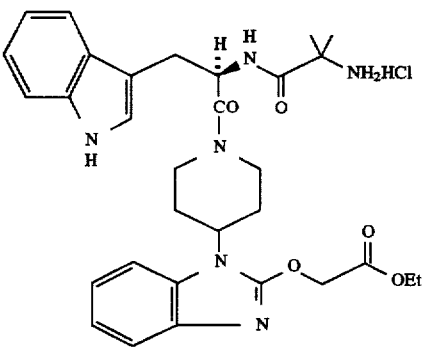

The intermediate prepared in Step B was treated with a saturated solution of dry HCl(gas) in EtOAc for 21 min at room temperature and the title compound was precipitated out with the addition of ether.

$^1$H NMR ($CD_3OD$, 400 MHz; mixture of rotamers) 7.85 and 7.55 (2 doublets, 1H), 7.35–6.60 (m, 8H), 5.37–5.15 (m, 1H), 4.73 and 4.65 (2bd, 1H), 4.60–4.50 (m, 2H), 4.42–4.00 (m, 3H), 3.63 and 3.52 (2 bd, 1H), 3.30–3.05 (m, 2H), 2.80–1.95 (m, 4H), 1.83-1.60 (m, 1H), 1.51, 1.50 and 1.48 (3S, 6H), 1.23 (2q, 3H), 1.05 and 1.66 (m, 1H).

EXAMPLE 10

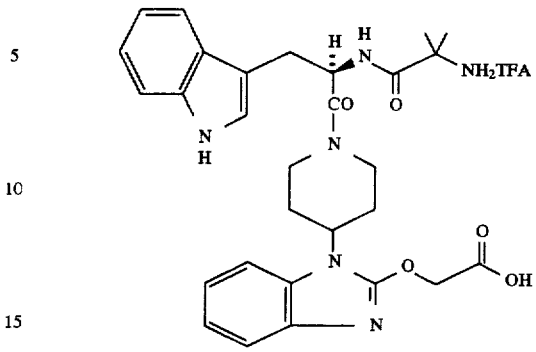

To a solution of 0.095 g of the ester intermediate prepared in Step B of Example 9 in 1 mL of THF-water (2:1) was added 0.015 g of lithium hydroxide monohydrate and stirred at room temperature for 30 min. The reaction mixture was acidified to pH=1 with 0.50N aqueous HCl and extracted with chloroform (2×5 mL). The combined organics were washed with aqueous saturated $NaHCO_3$ solution, dried over $MgSO_4$ and concentrated to give the acid that was deprotected by treatment with TFA to give the title compound.

$^1$H NMR ($CD_3OD$, 400 MHz; mixture of rotamers) 7.85 and 7.55 (2 doublets, 1H), 7.35–6.60 (m, 8H), 5.37–5.15 (m, 1H), 4.73 and 4.65 (2bd, 1H), 4.60–4.50 (m, 2H), 4.10–4.00 (m, 1H), 3.63 and 3.52 (2 bd, 1H), 3.30–3.05 (m, 2H), 2.80–1.95 (m, 4H), 1.83–1.60 (m, 1H), 1.51, 1.50 and 1.48 (3S, 6H), 1.05 and 1.66 (m, 1H).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

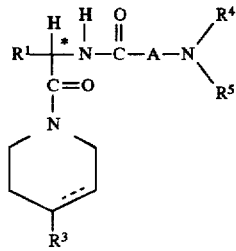

wherein:

$R^1$ is selected from the group consisting of: $C_1$–$C_{10}$ alkyl, aryl, aryl($C_1$–$C_6$ alkyl), ($C_3$–$C_7$ cycloalkyl)($C_1$–$C_6$ alkyl)-, ($C_1$–$C_5$ alkyl)-K-($C_1$–$C_5$ alkyl)-, aryl($C_0$–$C_5$ alkyl)-K-($C_1$–$C_5$ alkyl)-, and ($C_3$–$C_7$ cycloalkyl)($C_0$–$C_5$ alkyl)-K-($C_1$–$C_5$ alkyl)-, where K is —O—, —S(O)$_m$—, —N($R^2$)C(O)—, —C(O)N($R^2$)—, —OC(O)—, —C(O)O—, —CR$^2$=CR$^2$—, or —C—C—, where aryl is selected from: phenyl, naphthyl, indolyl, azaindolyl, pyridyl, benzothienyl, benzofuranyl, thiazolyl, and benzimidazolyl, and $R^2$ and alkyl may be further substituted by 1 to 9 halogen, —S(O)$_m$R$^{2a}$, 1 to 3 of —OR$^{2a}$ or —C(O)OR$^2$a, and aryl may be further substituted by 1 to 3 of $C_1$–$C_6$ alkyl, 1 to 3 of halogen, 1 to 2 of —OR$^2$, methylenedioxy, —S(O)$_m$R$^2$, 1 to 2 of —CF$_3$, —OCF$_3$, nitro, —N($R^2$)C(O)($R^2$), —C(O)OR$^2$, —C(O)N($R^2$)($R^2$), —1H-tetrazol-5-yl, —SO$_2$N($R^2$)($R^2$), —N($R^2$)SO$_2$ phenyl, or —N($R^2$)SO$_2$R$^2$;

$R^2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or NR$^{3a}$;

$R^{2a}$ is hydrogen, or $C_1$–$C_6$ alkyl optionally substituted by phenyl;

$R^3$ is a heterocycle selected from the group consisting of:

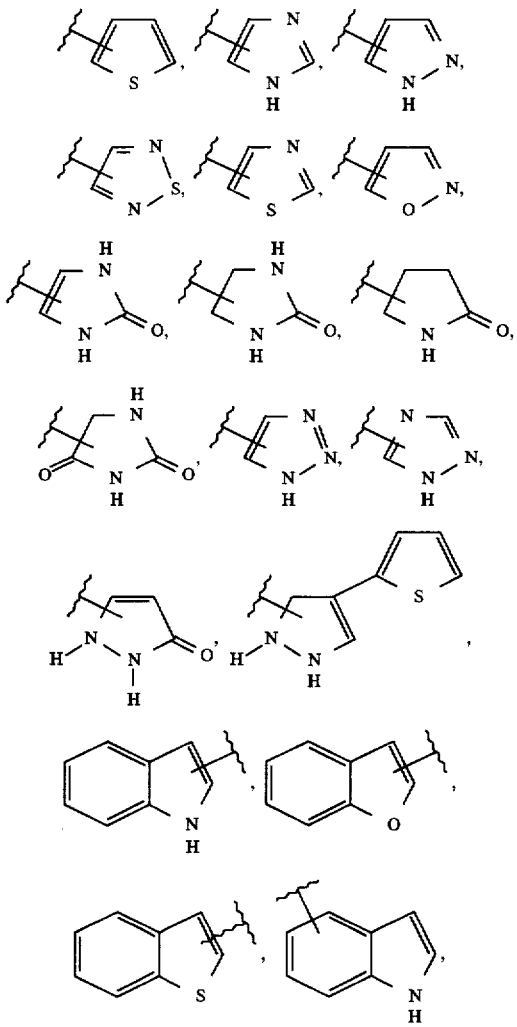

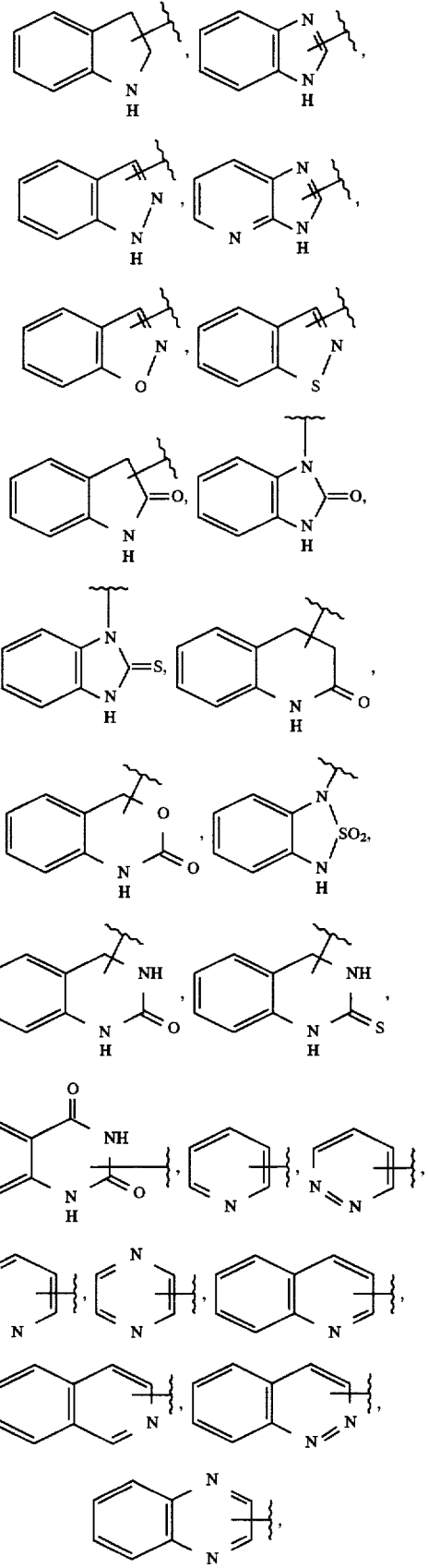

where the heterocycle is attached to the piperidine ring at an available nitrogen or carbon atom of the heterocycle, and where the heterocycle is optionally substituted on at least one available nitrogen or carbon atom by —R⁸, —OR⁸, —SR⁸, or —N(R²)(R⁸) where R⁸ is independently selected from the group consisting of:

hydrogen, C₁–C₆ alkyl, halogen, —OR², —OR⁶, —NHSO₂CF₃, —(CH₂)ᵣOR⁶, —(CH₂)ᵣN(R²)(R⁶), —(CH₂)ᵣ(R⁶), —(CH₂)ᵣC(O)OR², —(CH₂)ᵣC(O)OR⁶, —(CH₂)ᵣOC(O)R², —(CH₂)ᵣOC(O)R⁶, —(CH₂)ᵣC(O)R², —(CH₂)ᵣC(O)R⁶, (CH₂)ᵣC(O)N(R²)(R²), —(CH₂)ᵣC(O)N(R²)(R⁶), —(CH₂)ᵣN(R²)C(O)R² —(CH₂)ᵣN(R²)C(O)R⁶, —(CH₂)ᵣN(R⁶)C(O)R², —(CH₂)ᵣN(R⁶)C(O)R⁶, —(CH₂)ᵣN(R²)C(O)OR², —(CH₂)ᵣN(R²)C(O)OR⁶, —(CH₂)ᵣN(R⁶)C(O)OR², —(CH₂)ᵣN(R⁶)C(O)OR⁶, (CH₂)ᵣN(R²)C(O)N(R²)(R⁶), —(CH₂)ᵣN(R²)C(O)N(R²)(R²), —(CH₂)ᵣN(R⁶)C(O)N(R²)(R⁶), —(CH₂)ᵣN(R²)SO₂R⁶, —(CH₂)ᵣN(R⁶)SO₂R², —(CH₂)ᵣN(R²)SO₂R², —(CH₂)ᵣN(R⁶)SO₂R², —(CH₂)ᵣN(R⁶)SO₂R⁶, (CH₂)ᵣOC(O)N(R²)(R⁶), —(CH₂)ᵣOC(O)N(R²)(R²), —(CH₂)ᵣSO₂N(R²)(R⁶), —(CH₂)ᵣSO₂N(R²)(R²), —(CH₂)ᵣSO₂NHC(O)R⁶, —(CH₂)ᵣSO₂NHC(O)R², —(CH₂)ᵣSO₂NHC(O)OR⁶, —(CH₂)ᵣSO₂NHC(O)OR², —(CH₂)ᵣC(O)NHC(O)N(R²)(R⁶), —(CH₂)ᵣC(O)NHC(O)N(R²)(R²), —(CH₂)ᵣC(O)NHC(O)OR⁶, —(CH₂)ᵣCONHC(O)R², —(CH₂)ᵣCONHSO₂R⁶, —(CH₂)ᵣCONHSO₂R², —(CH₂)ᵣCONHSO₂N(R²)(R²), —(CH₂)ᵣCONHSO₂N(R²)(R⁶), —(CH₂)ᵣN(R²)SO₂N(R²)(R⁶), —(CH₂)ᵣN(R⁶)SO₂N(R²)(R²), —(CH₂)ᵣS(O)ₘR⁶, and —(CH₂)ᵣS(O)ₘR²;

R³ᵃ is hydrogen, or C₁–C₆ alkyl optionally substituted by hydroxyl;

R⁴ and R⁵ are independently hydrogen, C₁–C₆ alkyl, substituted C₁–C₆ alkyl where the substituents may be 1 to 5 halo, 1 to 3 hydroxy, 1 to 3 C₁–C₁₀ alkanoyloxy, 1 to 3 C₁–C₆ alkoxy, phenyl, phenoxy, 2-furyl, C₁–C₆ alkoxycarbonyl, S(O)ₘ(C₁–C₆ alkyl); or R⁴ and R⁵ can be taken together to form —(CH₂)ₐLₐ(CH₂)ₑ— where Lₐ is C(R²)₂, O, S(O)ₘ or N(R²), d and e are independently 1 to 3 and R² is as defined above;

A is:

$$-(CH_2)_x-\underset{R^{7a}}{\overset{R^7}{C}}-(CH_2)_y- \quad \text{or} \quad -Z-(CH_2)_x-\underset{R^{7a}}{\overset{R^7}{C}}-(CH_2)_y-$$

where x and y are independently 0, 1, 2 or 3;

Z is N-R⁶ᵃ or O, where R⁶ᵃ is hydrogen or C₁–C₆ alkyl;

R⁶ is hydrogen, C₁–C₆ alkyl, or (CH₂)ᵧaryl, wherein the alkyl and (CH₂)ᵧ groups may be optionally substituted by 1–2 O(R²), S(O)ₘR², 1H-tetrazol-5-yl, C(O)OR², C(O)N(R²)(R²) or SO₂N(R²)(R²), N(R²)C(O)N(R²)(R²), and where aryl is phenyl, pyridyl, 1H-tetrazol-5-yl, triazolyl, imidazolyl, thiazolyl, pyrazolyl, thiadiazolyl, imidazolone-1-yl, oxadiazolyl, benzimidazol-2-yl, triazolinone-yl, optionally substituted with C₁–C₆ alkyl, C₃–C₆ cycloalkyl, amino, or hydroxyl;

R⁷ and R⁷ᵃ are independently hydrogen, C₁–C₆ alkyl, trifluoromethyl, phenyl, substituted C₁–C₆ alkyl where the substituents are imidazolyl, phenyl, indolyl, p-hydroxyphenyl, OR², S(O)ₘR², C(O)OR², C₃–C₇ cycloalkyl, N(R²)(R²), C(O)N(R²)(R²); or R⁷ and R⁷ᵃ can independently be joined to one or both of R⁴ and R⁵ groups to form alkylene bridges between the terminal nitrogen and the alkyl portion of the R⁷ or R⁷ᵃ groups, wherein the bridge contains 1 to 5 carbons atoms;

or R⁷ and R⁷ᵃ can be joined to one another to form a C₃–C₇ cycloalkyl;

m is 0, 1, or 2;

r is 0, 1, 2, or 3;

v is 0, 1, or 2;

the dashed line indicates the presence of either a single bond or a double bond between the specified carbon atoms;

and pharmaceutically acceptable salts and individual diastereomers thereof.

2. The compound of claim 1 wherein:

R¹ is selected from the group consisting of: C₁–C₁₀ alkyl, aryl (C₁–C₄ alkyl)-, C₃–C₆ cycloalkyl (C₁–C₄ alkyl)-, (C₁–C₄ alkyl)-K-(C₁–C₂ alkyl)-, aryl (C₀–C₂ alkyl)-K-(C₁–C₂ alkyl)-, and (C₃–C₇ cycloalkyl)(C₀–C₂ alkyl)-K-(C₁–C₂ alkyl)-, where K is —O—, —S(O)ₘ—, —OC(O)—, or —C(O)O—, and the alkyl groups may be further substituted by 1 to 7 halogen, —S(O)ₘR², 1 to 3 —OR² or —C(O)OR², and aryl is phenyl, naphthyl, indolyl, pyridyl, benzimidazolyl, azaindolyl, benzothienyl or benzofuranyl which may be further substituted by 1 to 2 C₁–C₄ alkyl, 1 to 2 halogen, 1 to 2 —OR², —S(O)ₘR², or —C(O)OR²; R² is hydrogen, C₁–C₆ alkyl, C₃–C₇ cycloalkyl and where two C₁–C₆ alkyl groups are present on one atom they may be optionally joined to form a C₄–C₇ cyclic ring optionally including oxygen, sulfur or NR³ᵃ;

R³ is a heterocycle selected from the group consisting of:

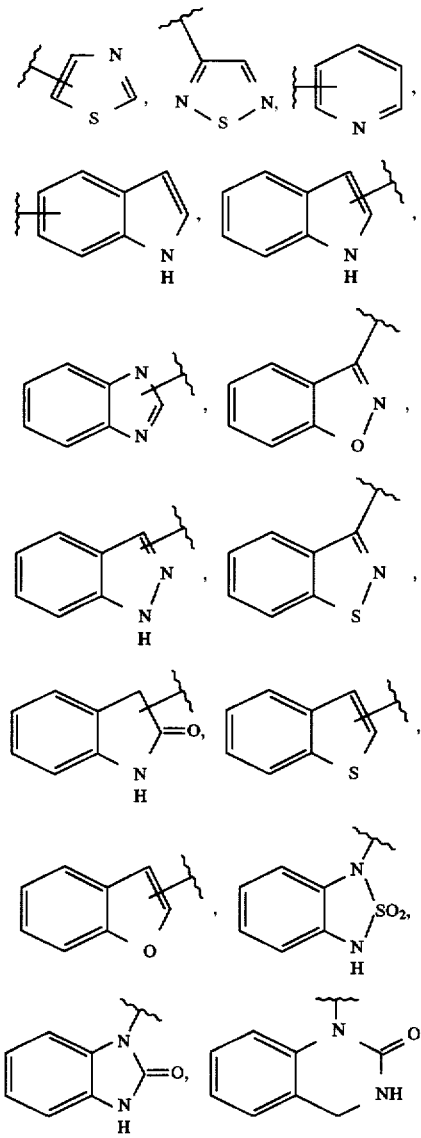

-continued

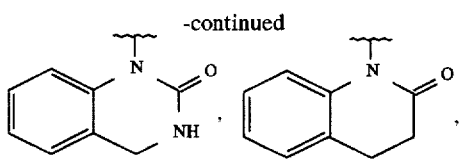

where the heterocycle is optionally substituted on at least one available nitrogen or carbon atom by —R$^8$ or —OR$^8$, where R$^8$ is independently selected from the group consisting of: hydrogen, C$_1$–C$_6$ alkyl, halogen, —OR$^2$, —OR$^6$, —NHSO$_2$CF$_3$, —(CH$_2$)$_r$OR$^6$, —(CH$_2$)$_r$N(R$^2$)(R$^6$), —(CH$_2$)$_r$(R$^6$), —(CH$_2$)$_r$C(0)OR$^2$, —(CH$_2$)$_r$C(O)OR$^6$, —(CH$_2$)$_r$OC(O)R$^2$, —(CH$_2$)$_r$OC(O)R$^6$, —(CH$_2$)$_r$C(O)R$^2$, —(CH$_2$)$_r$C(O)R$^6$, —(CH$_2$)$_r$C(O)N(R$^2$)(R$^2$), —(CH$_2$)$_r$C(O)N(R$^2$)(R$^6$), —(CH$_2$)$_r$N(R$^2$)C(O)R$^2$, —(CH$_2$)$_r$N(R$^2$)C(O)R$^6$, —(CH$_2$)$_r$N(R$^6$)C(O)R$^2$, —(CH$_2$)$_r$N(R$^6$)C(O)R$^6$, —(CH$_2$)$_r$N(R$^2$)C(O)OR$^2$, —(CH$_2$)$_r$N(R$^2$)C(O)OR$^6$, —(CH$_2$)$_r$N(R$^6$)C(O)OR$^2$, —(CH$_2$)$_r$N(R$^6$)C(O)OR$^6$, —(CH$_2$)$_r$N(R$^2$)C(O)N(R$^2$)(R$^6$), —(CH$_2$)$_r$N(R$^2$)C(O)N(R$^2$)(R$^2$), —(CH$_2$)$_r$N(R$^6$)C(O)N(R$^2$)(R$^6$), —(CH$_2$)$_r$N(R$^2$)SO$_2$R$^6$, —(CH$_2$)$_r$N(R$^2$)SO$_2$R$^2$, —(CH$_2$)$_r$N(R$^6$)SO$_2$R$^2$, —(CH$_2$)$_r$N(R$^6$)SO$_2$R$^6$, —(CH$_2$)$_r$OC(O)N(R$^2$)(R$^6$), —(CH$_2$)$_r$OC(O)N(R$^2$)(R$^2$), —(CH$_2$)$_r$SO$_2$N(R$^2$)(R$^6$), —(CH$_2$)$_r$SO$_2$N(R$^2$)(R$^2$), —(CH$_2$)$_r$SO$_2$NHC(O)R$^6$, —(CH$_2$)$_r$SO$_2$NHC(O)R$^2$, —(CH$_2$)$_r$SO$_2$NHC(O)OR$^6$, —(CH$_2$)$_r$SO$_2$NHC(O)OR$^2$, —(CH$_2$)$_r$C(O)NHC(O)N(R$^2$)(R$^6$), —(CH$_2$)$_r$C(O)NHC(O)N(R$^2$)(R$^2$), —(CH$_2$)$_r$C(O)NHC(O)R$^6$, —(CH$_2$)$_r$CONHCO(O)R$^2$, —(CH$_2$)$_r$CONHSO$_2$R$^6$, —(CH$_2$)$_r$CONHSO$_2$R$^2$, —(CH$_2$)$_r$CONHSO$_2$N(R$^2$)R$^2$), —(CH$_2$)$_r$CONHSO$_2$N(R$^2$)R$^6$), —(CH$_2$)$_r$N(R$^2$)SO$_2$N(R$^2$)R$^6$), —(CH$_2$)$_r$N(R$^6$)SO$_2$N(R$^2$)R$^6$), —(CH$_2$)$_r$S(O)$_m$R$^6$, and —(CH$_2$)$_r$S(O)$_m$R$^2$;

R$^{3a}$ is hydrogen, or C$_1$–C$_4$ alkyl;

R$^4$ and R$^5$ are independently hydrogen, C$_1$–C$_6$ alkyl, or substituted C$_1$–C$_6$ alkyl where the substituents may be 1 to 5 halo, 1 to 3 hydroxyl, S(O)$_m$(C$_1$–C$_6$ alkyl) or phenyl;

R$^6$ is H, C$_1$–C$_6$ alkyl, or (CH$_2$)$_v$aryl, wherein the (CH$_2$)$_v$ and alkyl groups may be optionally substituted by 1–2 O(R$^2$), S(O)$_m$R$^2$, C(O)OR$^2$, C(O)N(R$^2$)(R$^2$) or SO$_2$N(R$^2$)(R$^2$), N(R$^2$)C(O)N(R$^2$)(R$^2$), wherein the aryl group is selected from: phenyl, pyridyl, 1H-tetrazol-5-yl, triazolyl, imidazolyl, thiazolyl, oxadiazolyl, pyrazolyl, thiadiazolyl, and benzimidazol-2-yl, which is optionally substituted with C$_1$–C$_6$ alkyl, C$_3$–C$_6$ cycloalkyl, amino, or hydroxyl;

A is:

(CH$_2$)x—C—
|
R$^7$
|
R$^{7a}$ where x is 0, or 1;

R$^7$ and R$^{7a}$ are independently hydrogen C$_1$–C$_6$ alkyl, trifluoromethyl, phenyl, substituted C$_1$–C$_6$ alkyl where the substituents are imidazolyl, phenyl, indolyl, p-hydroxyphenyl, OR$^2$, S(O)$_m$R$^2$, C(O)OR$^2$, C$_5$–C$_7$ cycloalkyl, N(R$^2$)(R$^2$), C(O)N(R$^2$)(R$^2$); or R$^7$ and R$^{7a}$ can independently be joined to one of R$^4$ or R$^5$ to form alkylene bridges between the terminal nitrogen and the alkyl portion of R$^7$ or R$^{7a}$ groups to form 5 or 6 membered rings; or R$^7$ and R$^{7a}$ can be joined to one another to form a C$_3$ cycloalkyl;

m is 0, 1,or2;

r is 0, 1, 2,or3;

v is 0, 1, or 2;

the dashed line indicates the presence of either a single bond or a double bond between the specified carbon atoms;

and pharmaceutically acceptable salts and individual diastereomers thereof.

3. The compound of claim 1 of the formula:

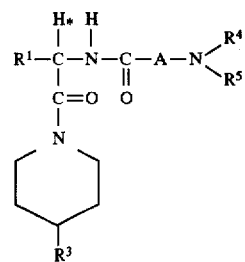

where R$^1$, R$^3$, R$^4$, R$^5$, A and the dashed line are as defined in claim 1.

4. The stereospecifically defined compound of claim 1 of the formula:

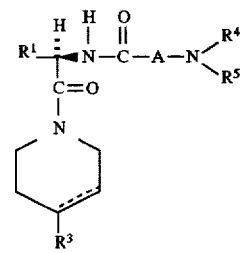

5. A compound which is selected from the group consisting of:

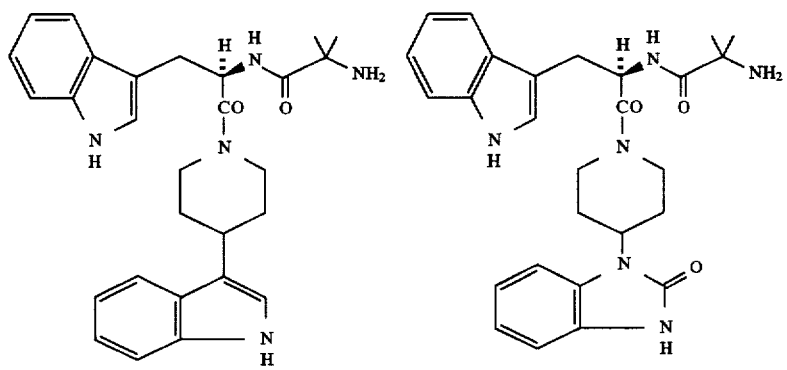

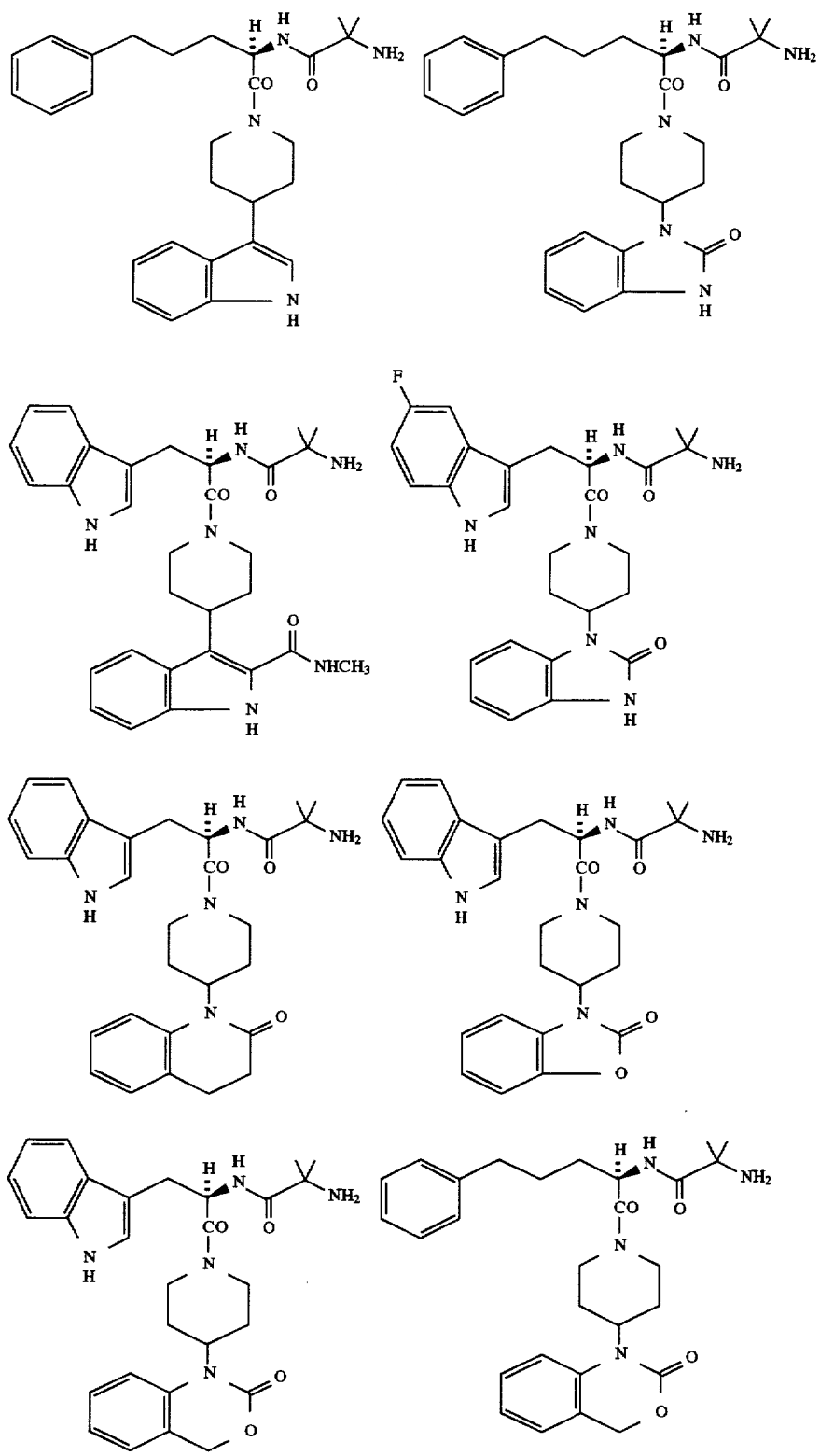

-continued
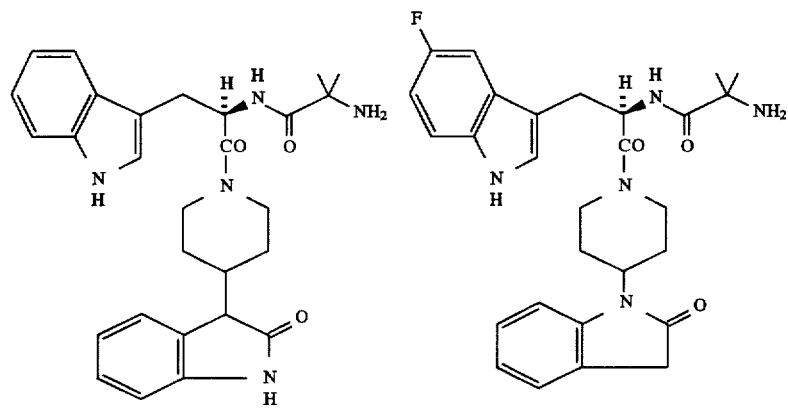
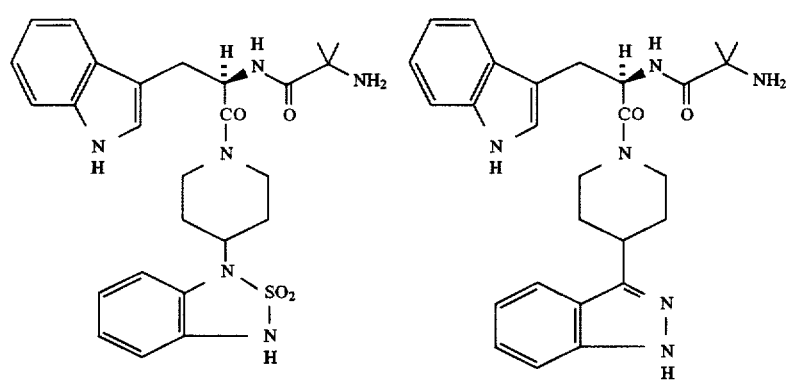
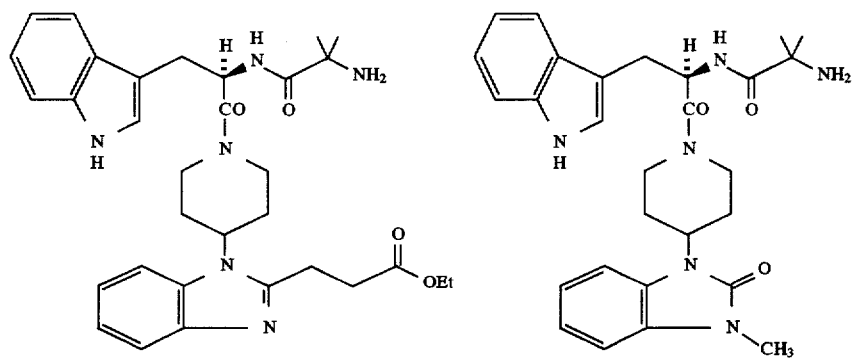
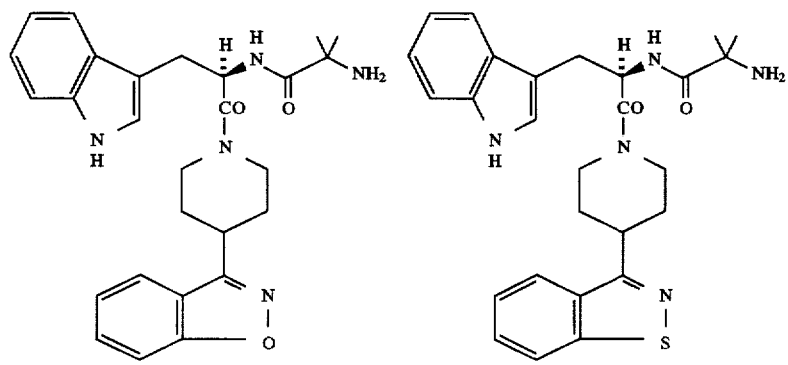

-continued

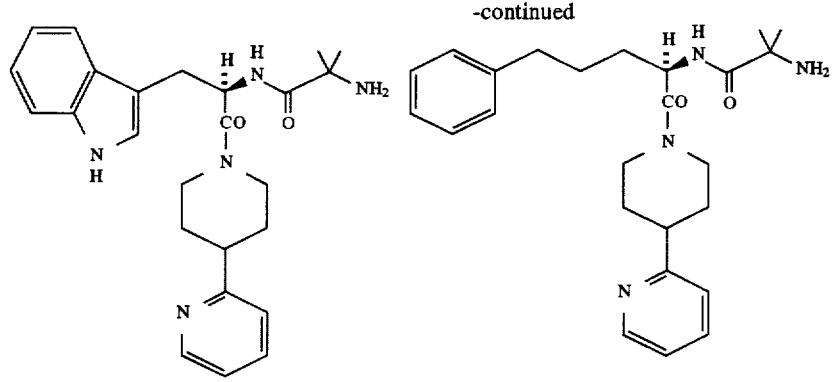

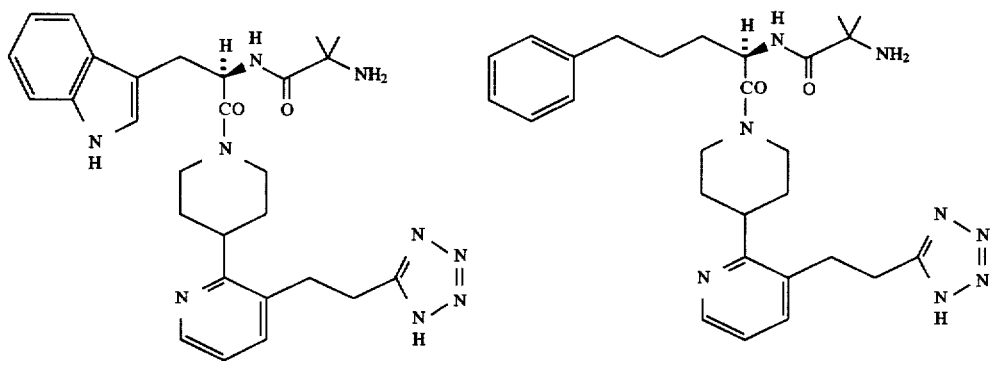

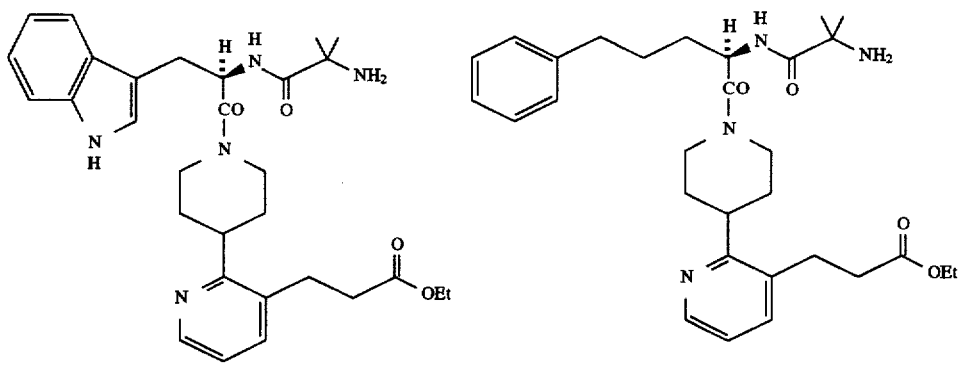

and their pharmaceutically acceptable salts and individual diasteromers thereof where not otherwise specified.

6. A composition useful for increasing the endogenous production or release of growth hormone in a human or an animal which comprises an inert carrier and an effective amount of a compound of claim 1.

7. A composition useful for increasing the endogenous production or release of growth hormone in a human or an animal which comprises an inert carrier and an effective amount of a compound of claim 1 in combination with an additional growth hormone secretagogue.

8. The composition of claim 7 wherein the additional growth hormone secretagogue is selected from the group consisting of: growth hormone releasing peptide GHRP-6; growth hormone releasing peptide GHRP-2; growth hormone releasing peptide GHRP-1; B-HT920; growth hormone releasing factor; an analog of growth hormone releasing factor; IGF-1 and IGF-2.

9. A composition useful for the treatment of osteoporosis which comprises a combination of a bisphosphonate compound and a compound of claim 1.

10. The composition of claim 9 wherein the bisphosphonate compound is alendronate.

11. A method for increasing levels of endogenous growth hormone in a human or an animal which comprises administering to such human or animal an effective amount of a compound of claim 1.

* * * * *